US011590262B2

(12) United States Patent
Greenhalgh

(10) Patent No.: US 11,590,262 B2
(45) Date of Patent: Feb. 28, 2023

(54) SURGICAL REPAIR GRAFT

(71) Applicant: TELA Bio, Inc., Malvern, PA (US)

(72) Inventor: E. Skott Greenhalgh, Gladwyne, PA (US)

(73) Assignee: TELA BIO, INC., Malvern, PA (US)

( * ) Notice: Subject to any disclaimer, the term of this patent is extended or adjusted under 35 U.S.C. 154(b) by 42 days.

(21) Appl. No.: 16/979,150

(22) PCT Filed: Mar. 8, 2019

(86) PCT No.: PCT/US2019/021484
§ 371 (c)(1),
(2) Date: Sep. 8, 2020

(87) PCT Pub. No.: WO2019/173792
PCT Pub. Date: Sep. 12, 2019

(65) Prior Publication Data
US 2020/0397949 A1 Dec. 24, 2020

Related U.S. Application Data

(60) Provisional application No. 62/641,125, filed on Mar. 9, 2018.

(51) Int. Cl.
A61L 27/52 (2006.01)
A61L 27/24 (2006.01)
A61L 27/54 (2006.01)
A61L 27/58 (2006.01)

(52) U.S. Cl.
CPC .............. A61L 27/52 (2013.01); A61L 27/24 (2013.01); A61L 27/54 (2013.01); A61L 27/58 (2013.01); A61L 2300/626 (2013.01); A61L 2430/34 (2013.01)

(58) Field of Classification Search
CPC .......... A61L 27/52; A61L 27/24; A61L 27/54; A61L 27/58; A61L 2300/626; A61L 2430/34; A61L 31/044; A61L 31/145; A61L 31/146; A61L 31/148; A61L 31/16; A61L 2300/402; A61L 2300/404; A61L 2300/406; A61L 2300/416; A61L 2430/04; A61L 27/56; B32B 5/18; B32B 5/245; B32B 5/26; B32B 7/09; B32B 7/12; B32B 9/02; B32B 2266/122; B32B 27/36; B32B 9/047; B32B 27/12; B32B 27/28; B32B 2250/02; B32B 2255/02; B32B 2255/24; B32B 2262/08; B32B 2266/06; B32B 2266/08; B32B 2307/538; B32B 2307/546; B32B 2307/7163; B32B 2307/72; B32B 2307/732; B32B 2535/00; B32B 3/266; B32B 5/028; A61K 9/127
See application file for complete search history.

(56) References Cited

U.S. PATENT DOCUMENTS

| 2,259,025 | A | 10/1941 | Cosgro |
| 3,033,139 | A | 5/1962 | Tateishi |
| 3,054,406 | A | 9/1962 | Usher |
| 3,155,095 | A | 3/1964 | Brown |
| 3,364,200 | A | 1/1968 | Ashton et al. |
| 5,593,441 | A | 1/1997 | Lichtenstein et al. |
| 5,634,931 | A | 6/1997 | Kugel |
| 5,683,400 | A | 11/1997 | McGuire |
| 5,707,395 | A | 1/1998 | Li |
| 5,919,232 | A | 7/1999 | Chaffringeon et al. |
| 5,990,378 | A | 11/1999 | Ellis |
| 6,120,539 | A | 9/2000 | Eldridge et al. |
| 6,258,124 | B1 | 7/2001 | Darois et al. |
| 6,319,264 | B1 | 11/2001 | Törmälä et al. |
| 6,371,985 | B1 | 4/2002 | Goldberg |
| 6,383,201 | B1 | 5/2002 | Dong |
| 6,652,595 | B1 | 11/2003 | Nicolo |
| 6,814,748 | B1 | 11/2004 | Baker et al. |
| 6,962,120 | B1 | 11/2005 | Fujikura et al. |
| 7,824,420 | B2 | 11/2010 | Eldridge et al. |
| 7,946,236 | B2 | 5/2011 | Butcher |
| 8,074,591 | B2 | 12/2011 | Butcher et al. |
| 8,182,545 | B2 | 5/2012 | Cherok et al. |
| 8,236,342 | B2 | 8/2012 | Thomas et al. |
| 8,853,294 | B2 | 10/2014 | Myung et al. |

(Continued)

FOREIGN PATENT DOCUMENTS

| DE | 10312674 A1 | 10/2003 |
| DE | 112007001732 T5 | 4/2011 |

(Continued)

OTHER PUBLICATIONS

Deeken et al., Physiocomechanical evaluation of absorbable and nonabsorbable barrier composite meshes for laparoscopic ventral hernia repair. Surg. Endosc., 25(5), 1541-1552 ( 12 pages, Author Manuscript); May 2011.
Franklin et al.; Uptake of tetracycline by aortic aneurysm wall and its effect on inflammation and proteolysis; British Journal of Surgery; 86(6); pp. 771-775; Jun. 1999.
Mayo Clinic;Placement of Breast Implants; retrieved May 25, 2017 from http://www.mayoclinic.org/placement-of-breast-implants/img-20007384; 1 pg; May 25, 2017.
Pyo et al.; Targeted gene disruption of matrix metalloproteinase-9 (gelatinase B) suppresses development of experimental abdominal aortic aneurysms; The journal of Clinical Investigation; 105(11); pp. 1641-1649; Jun. 2000.

(Continued)

Primary Examiner — Robert A Wax
Assistant Examiner — Quanglong N Truong
(74) Attorney, Agent, or Firm — Shay Glenn LLP

(57) ABSTRACT

The apparatuses and methods described herein relates generally to the field of active agent (drug) release from surgical grafts useful for soft tissue reconstruction, regeneration, or repair. More particularly, described herein are surgical grafts for soft tissue repair that include active agent that is released over time while advantageously matching the biomechanical properties of tissue during healing and recovery.

26 Claims, 12 Drawing Sheets

(56) References Cited

U.S. PATENT DOCUMENTS

| | | |
|---|---|---|
| 9,205,052 B2 | 12/2015 | Kim et al. |
| 9,289,279 B2 | 3/2016 | Wilson et al. |
| 9,295,757 B2 | 3/2016 | Patel et al. |
| 9,326,840 B2 | 5/2016 | Mortarino |
| 9,364,310 B2 | 6/2016 | Stopek |
| 9,421,079 B2 | 8/2016 | Koullick et al. |
| 9,468,705 B2 | 10/2016 | Geller |
| 9,510,925 B2 | 12/2016 | Hotter et al. |
| 9,554,887 B2 | 1/2017 | Lecuivre |
| 9,585,838 B2 | 3/2017 | Hartounian et al. |
| 9,770,414 B2 | 9/2017 | Garcia et al. |
| 9,775,700 B2 | 10/2017 | Greenhalgh et al. |
| 9,820,843 B2 | 11/2017 | Greenhalgh et al. |
| 9,925,030 B2 | 3/2018 | Greenhalgh et al. |
| 10,130,457 B2 | 11/2018 | Greenhalgh et al. |
| 10,213,284 B2 | 2/2019 | Greenhalgh et al. |
| 10,426,587 B2 | 10/2019 | Greenhalgh et al. |
| 10,500,030 B2 | 12/2019 | Greenhalgh et al. |
| 10,561,485 B2 | 2/2020 | Greenhalgh et al. |
| 10,675,141 B2 | 6/2020 | Greenhalgh et al. |
| 10,702,364 B2 | 7/2020 | Greenhalgh et al. |
| 2001/0020188 A1 | 9/2001 | Sander |
| 2002/0111392 A1 | 8/2002 | Cruise |
| 2003/0023316 A1 | 1/2003 | Brown et al. |
| 2003/0225355 A1 | 12/2003 | Butler |
| 2004/0010320 A1 | 1/2004 | Huckle et al. |
| 2004/0033212 A1 | 2/2004 | Thomson et al. |
| 2004/0054376 A1 | 3/2004 | Ory et al. |
| 2004/0078089 A1 | 4/2004 | Ellis et al. |
| 2004/0138762 A1 | 7/2004 | Therin et al. |
| 2004/0249457 A1 | 12/2004 | Smith et al. |
| 2005/0070930 A1 | 3/2005 | Kammerer |
| 2005/0113849 A1 | 5/2005 | Popadiuk et al. |
| 2005/0113938 A1 | 5/2005 | Jamiolkowski et al. |
| 2005/0118236 A1 | 6/2005 | Qiu et al. |
| 2005/0255543 A1 | 11/2005 | Just et al. |
| 2006/0178683 A1 | 8/2006 | Shimoji et al. |
| 2006/0217747 A1 | 9/2006 | Ferree |
| 2006/0229722 A1 | 10/2006 | Bianchi et al. |
| 2007/0088434 A1 | 4/2007 | Frank |
| 2007/0190108 A1 | 8/2007 | Datta et al. |
| 2007/0224238 A1 | 9/2007 | Mansmann et al. |
| 2008/0097601 A1 | 4/2008 | Codori-Hurff et al. |
| 2008/0167729 A1 | 7/2008 | Nelson et al. |
| 2008/0181928 A1 | 7/2008 | Hakimi-Mehr et al. |
| 2009/0018655 A1 | 1/2009 | Brunelle et al. |
| 2009/0054339 A1 | 2/2009 | Marshal et al. |
| 2009/0069893 A1* | 3/2009 | Paukshto ............... A61L 27/24 428/221 |
| 2009/0082864 A1 | 3/2009 | Chen et al. |
| 2009/0216338 A1 | 8/2009 | Gingras et al. |
| 2009/0306688 A1 | 12/2009 | Patel et al. |
| 2009/0326577 A1 | 12/2009 | Johnson et al. |
| 2010/0010114 A1 | 1/2010 | Myung et al. |
| 2010/0028396 A1 | 2/2010 | Ward et al. |
| 2010/0063599 A1 | 3/2010 | Brunelle et al. |
| 2010/0100107 A1 | 4/2010 | Duggal et al. |
| 2010/0120679 A1 | 5/2010 | Xu et al. |
| 2010/0217388 A1 | 8/2010 | Cohen et al. |
| 2010/0249929 A1 | 9/2010 | Kurz et al. |
| 2010/0305500 A1 | 12/2010 | Lambert et al. |
| 2010/0318108 A1 | 12/2010 | Datta et al. |
| 2010/0318124 A1 | 12/2010 | Leung et al. |
| 2011/0014153 A1 | 1/2011 | Derwin et al. |
| 2011/0125287 A1 | 5/2011 | Hotter et al. |
| 2011/0196490 A1 | 8/2011 | Gadikota et al. |
| 2011/0250264 A1 | 10/2011 | Schutt et al. |
| 2011/0257761 A1 | 10/2011 | Mortarino |
| 2011/0301717 A1 | 12/2011 | Becker |
| 2012/0010637 A1 | 1/2012 | Stopek et al. |
| 2012/0035608 A1 | 2/2012 | Marchitto et al. |
| 2012/0082712 A1 | 4/2012 | Stopek et al. |
| 2012/0095482 A1 | 4/2012 | Peterson et al. |
| 2012/0143329 A1 | 6/2012 | Kim |
| 2012/0165957 A1 | 6/2012 | Everland et al. |
| 2012/0179176 A1 | 7/2012 | Wilson et al. |
| 2012/0184974 A1 | 7/2012 | Becker |
| 2012/0253464 A1 | 10/2012 | Hwang et al. |
| 2013/0064772 A1 | 3/2013 | Swiss et al. |
| 2013/0116799 A1 | 5/2013 | Derwin et al. |
| 2013/0172994 A1 | 7/2013 | Becker |
| 2013/0197300 A1 | 8/2013 | Koullick et al. |
| 2013/0209547 A1 | 8/2013 | Garcia et al. |
| 2013/0211307 A1 | 8/2013 | Evans et al. |
| 2013/0267137 A1 | 10/2013 | Peniston et al. |
| 2013/0303958 A1 | 11/2013 | Holm et al. |
| 2013/0304098 A1 | 11/2013 | Mortarino |
| 2013/0317286 A1 | 11/2013 | Bluecher et al. |
| 2014/0094931 A1 | 4/2014 | Derwin et al. |
| 2014/0276993 A1 | 9/2014 | Reilly et al. |
| 2014/0364878 A1 | 12/2014 | Ladet et al. |
| 2015/0112434 A1 | 4/2015 | Felix et al. |
| 2015/0127103 A1 | 5/2015 | Seedhom |
| 2015/0267330 A1 | 9/2015 | Carrier et al. |
| 2015/0297798 A1 | 10/2015 | Badylak et al. |
| 2016/0058534 A1 | 3/2016 | Derwin et al. |
| 2016/0058589 A1 | 3/2016 | Bar et al. |
| 2016/0136289 A1 | 5/2016 | Puri et al. |
| 2016/0206580 A1 | 7/2016 | Los et al. |
| 2016/0262208 A1 | 9/2016 | Hsieh |
| 2016/0374791 A1 | 12/2016 | Lecuivre et al. |
| 2017/0027679 A1 | 2/2017 | Serban et al. |
| 2017/0086972 A1 | 3/2017 | Braido et al. |
| 2017/0245847 A1 | 8/2017 | Obermiller |
| 2019/0008623 A1 | 1/2019 | Nemoto et al. |
| 2019/0183624 A1 | 6/2019 | Greenhalgh et al. |
| 2019/0380822 A1 | 12/2019 | Greenhalgh et al. |
| 2020/0253707 A1 | 8/2020 | Greenhalgh et al. |
| 2020/0281707 A1 | 9/2020 | Greenhalgh et al. |
| 2020/0297476 A1 | 9/2020 | Greenhalgh et al. |
| 2020/0330211 A1 | 10/2020 | Greenhalgh et al. |
| 2020/0360129 A1 | 11/2020 | Moses et al. |
| 2021/0030925 A1 | 2/2021 | Lopez et al. |
| 2021/0093444 A1 | 4/2021 | Feinberg et al. |
| 2021/0290416 A1 | 9/2021 | Hall et al. |
| 2022/0110749 A1 | 4/2022 | Hariton et al. |

FOREIGN PATENT DOCUMENTS

| | | |
|---|---|---|
| EP | 2198854 A2 | 6/2010 |
| EP | 2229918 A1 | 9/2010 |
| EP | 2300066 A2 | 3/2011 |
| EP | 2344133 A2 | 7/2011 |
| RU | 2524196 C2 | 7/2014 |
| WO | WO00/57812 A1 | 10/2000 |
| WO | WO02/078568 A1 | 10/2002 |
| WO | WO03/082363 A1 | 10/2003 |
| WO | WO03/094781 A1 | 11/2003 |
| WO | WO2008/095038 A1 | 8/2008 |
| WO | WO2012/017415 A2 | 2/2012 |
| WO | WO2017/050837 A1 | 3/2017 |
| WO | WO2017/191276 A1 | 11/2017 |
| WO | WO2017/223462 A1 | 12/2017 |

OTHER PUBLICATIONS

Tambiah et al.; Provocation of experimental aortic inflammation and dilatation by inflammatory mediators and chlamydia pneumoniae; British Journal of Surgery; 88(7); pp. 935-940; Jul. 2001.

Walton et al.; Inhibition of prostoglandin E2 synthesis in abdonminal aortic; Circulation; 100; pp. 48-54; 8 pages; Jul. 1999.

XU et al.; Sp1 increases expression of cyclooxygenase-2 in hypoxic vascular endothelium implications for the mechanisms of aortic aneurysm and heart failure; journal of Biological Chemistry; 275(32); p. 24583-24589; Aug. 2000.

Greenhalgh et al.; U.S. Appl. No. 17/710,671 entitled "Corner-lock stitch patterns," filed Mar. 31, 2022.

\* cited by examiner

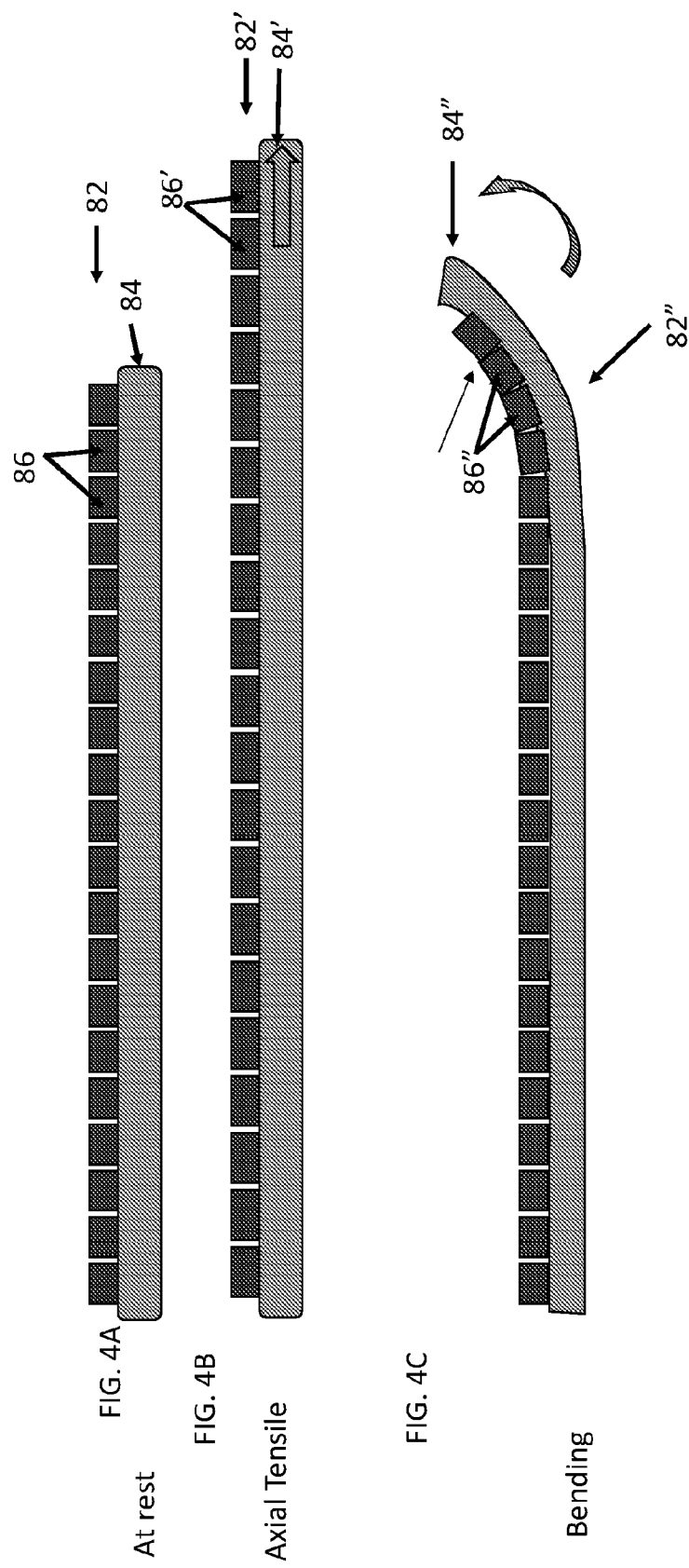

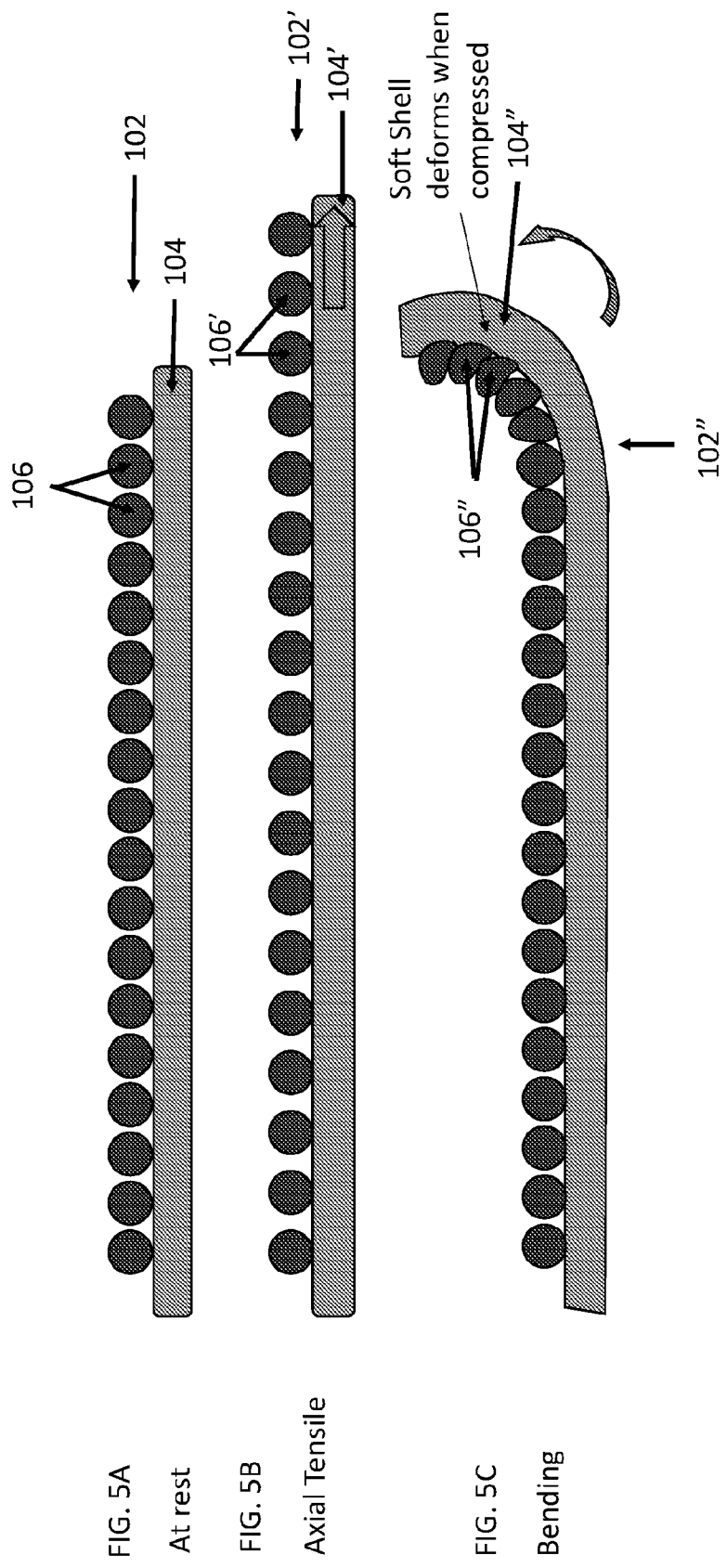

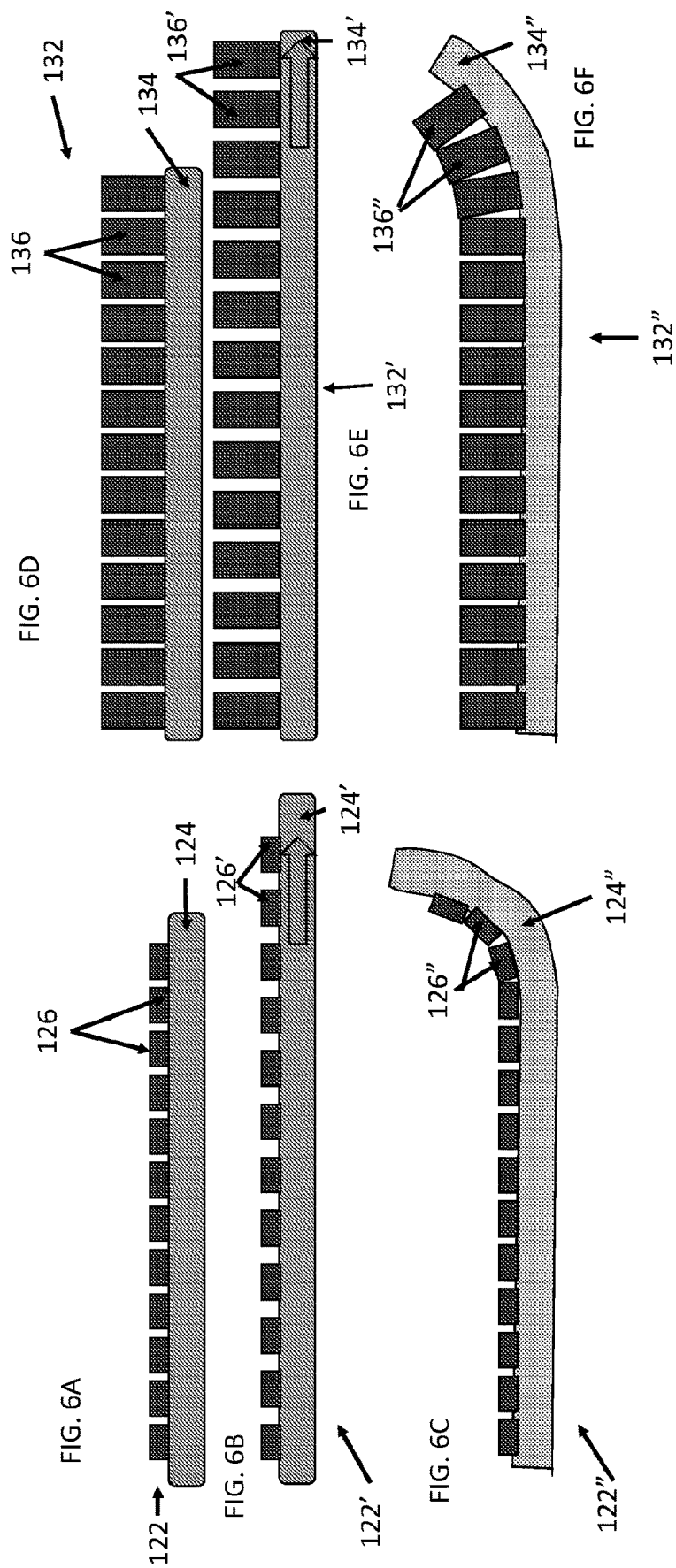

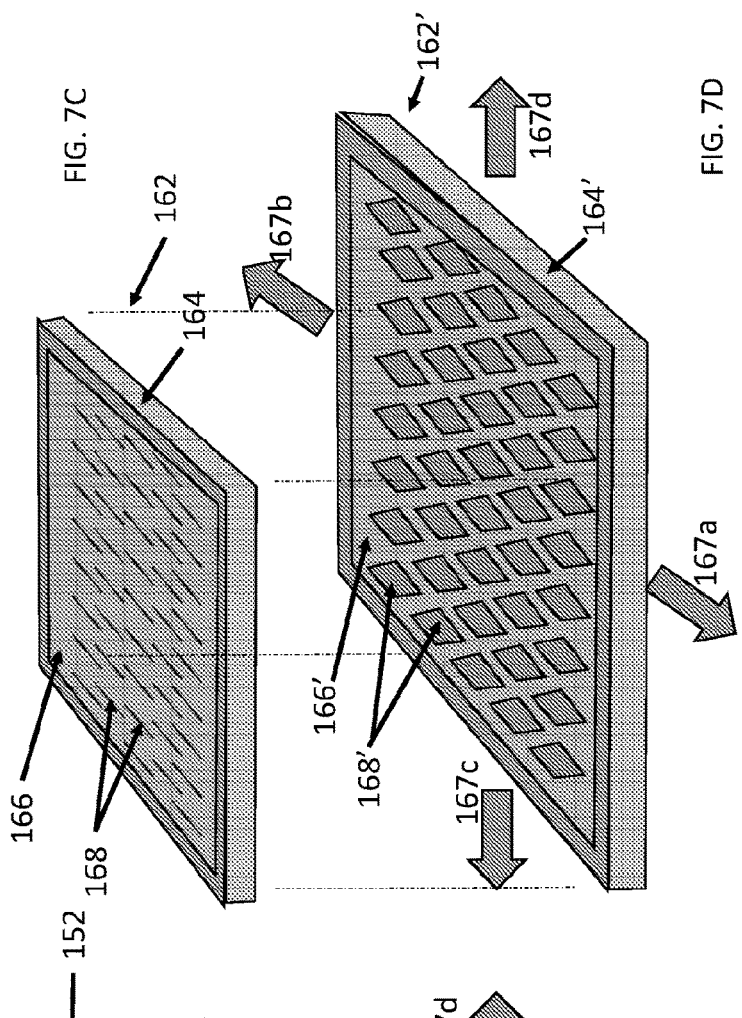
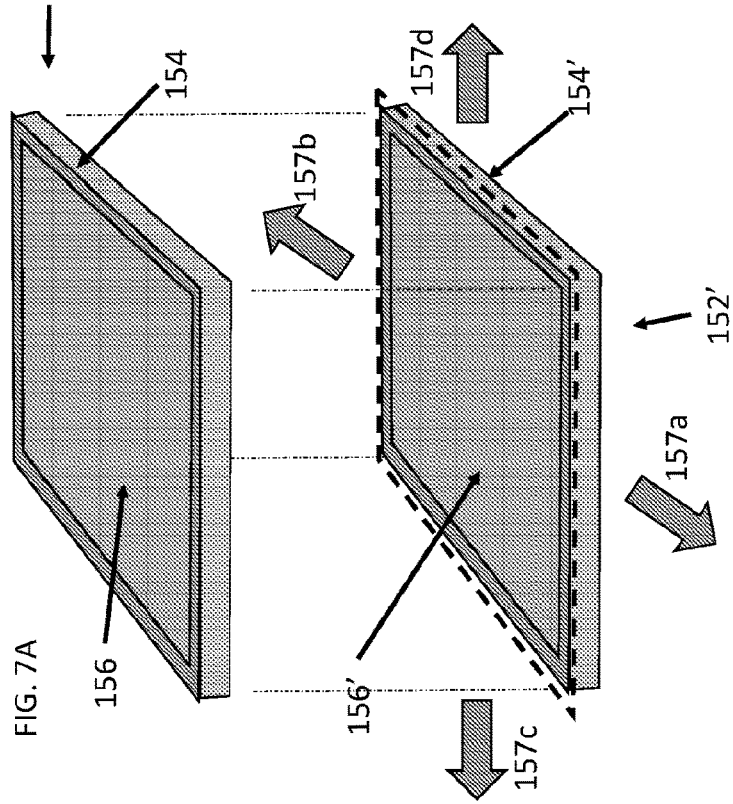

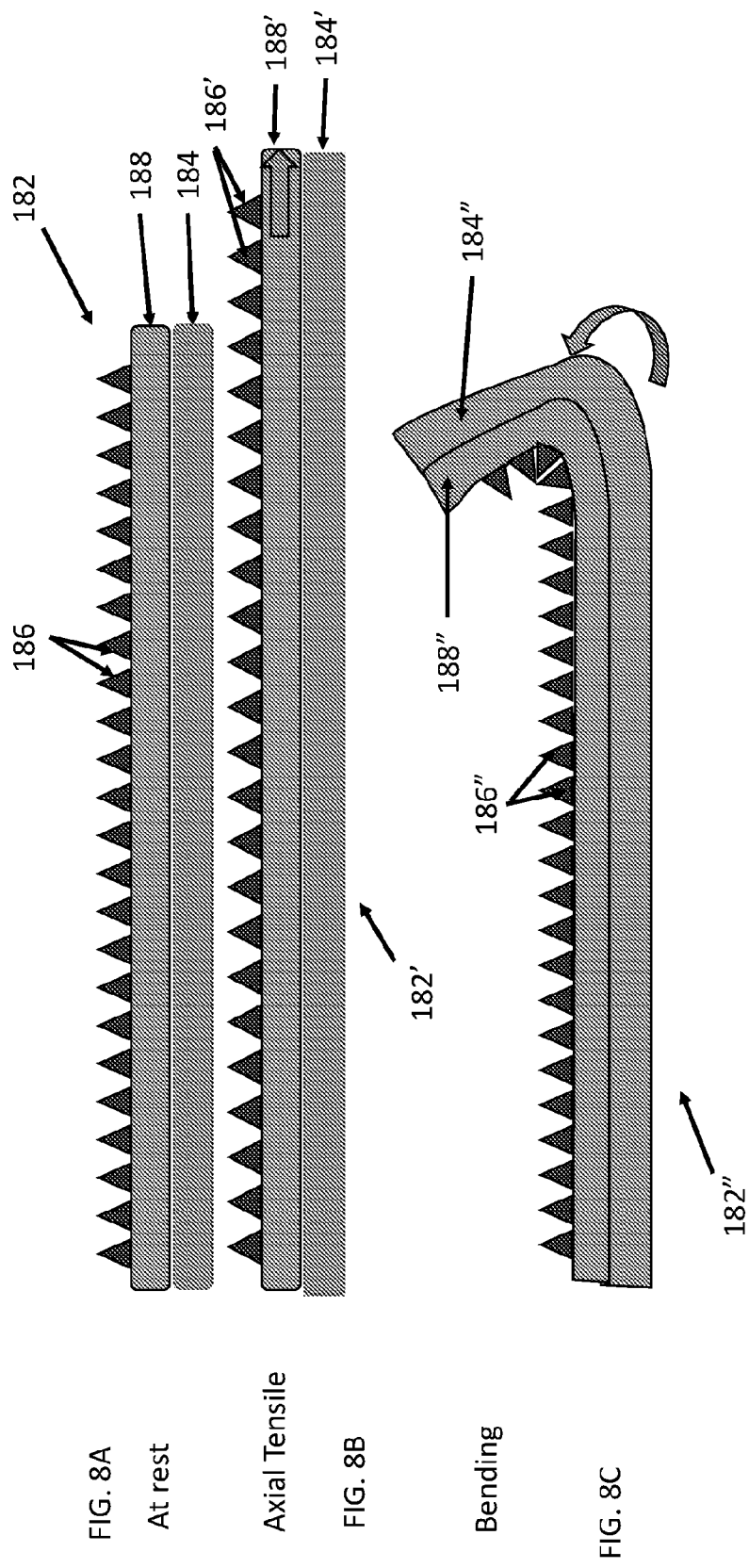

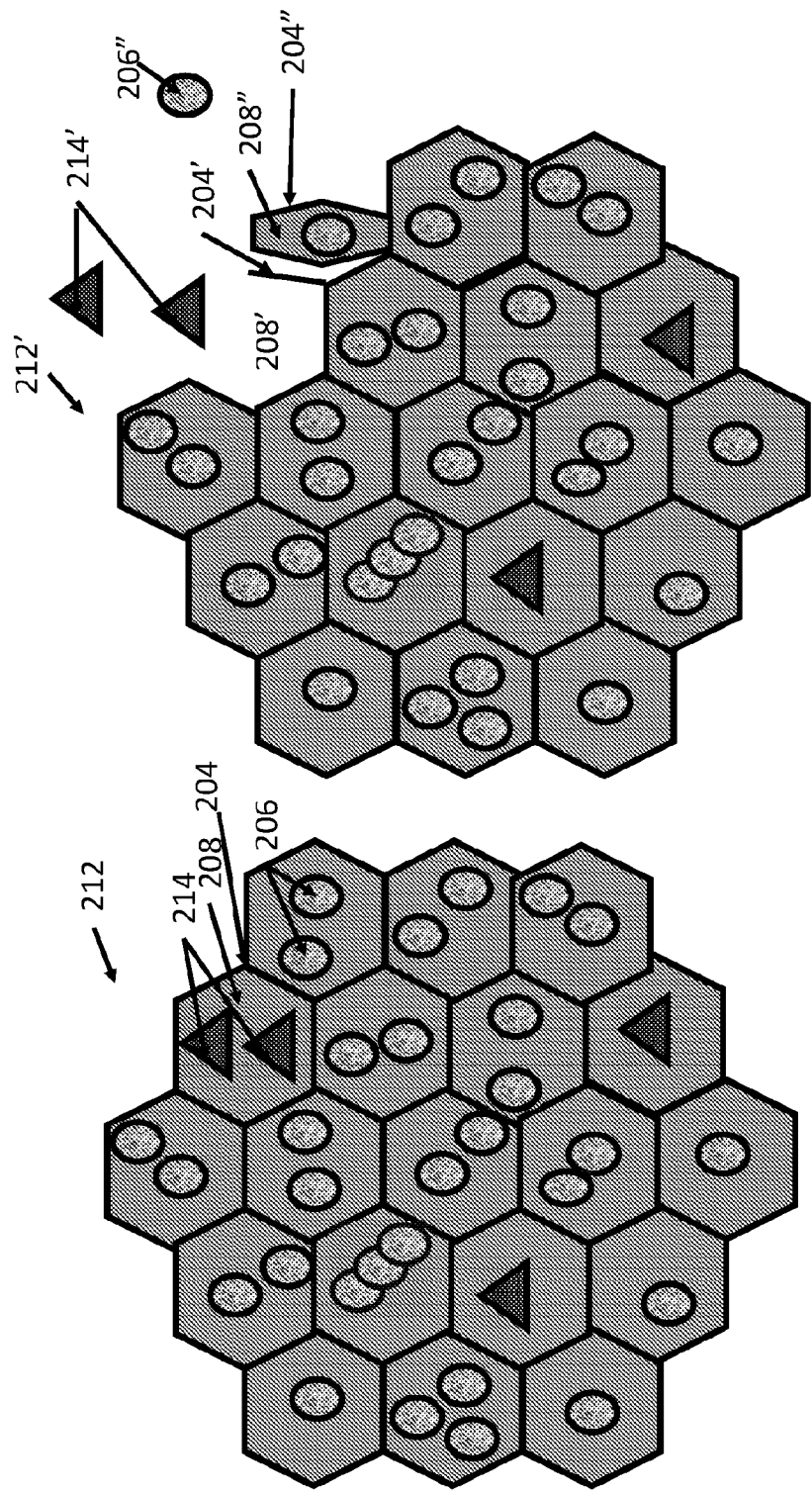

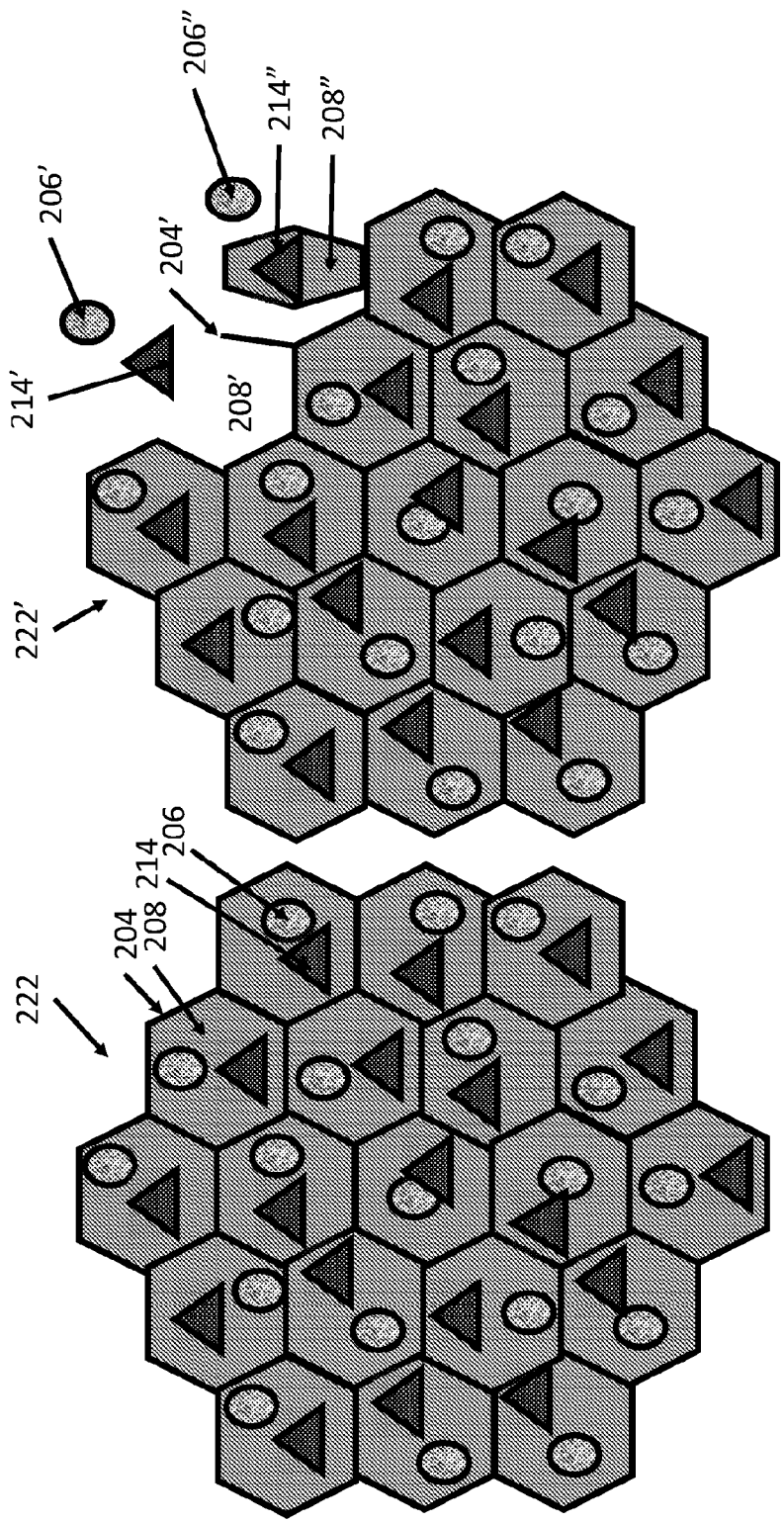

SURGICAL REPAIR GRAFT

CROSS REFERENCE TO RELATED APPLICATIONS

This patent application is a 371 of International Patent Application No. PCT/US2019/021484, titled "SURGICAL REPAIR GRAFTS," filed in Mar. 8, 2019, now International Publication No. WO 2019/173792, which claims priority to U.S. Provisional Patent Application No. 62/641,125, titled "SURGICAL REPAIR GRAFT," filed on Mar. 9, 2018, and herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The apparatuses and methods described herein relates generally to the field of active agent (drug) release from surgical grafts and medical textiles useful for soft tissue reconstruction, regeneration, or repair. More particularly, described herein are surgical repair grafts and medical textiles for soft tissue repair that include an active agent that is released over time while advantageously matching the biomechanical properties of tissue during healing and recovery.

BACKGROUND

Soft tissues within a body may benefit from repair or reinforcement due to a variety of reasons such as disease, enhancement, or trauma.

An implant or medical textile may be used to repair or reinforce a soft tissue such as an unhealthy or modified tissue in the body. The tissue may be, for example, tissue that is no longer able to maintain its shape or physiological function such as a hernia or a tissue for which a shape or size change is desired such as breast size or shape change due to breast enhancement or breast reconstruction. A hernia is a condition in which part of an organ or fatty tissue protrudes through the wall of a surrounding tissue. Abdominal wall hernia surgery is one of the most common surgical procedures, and according to the U.S. Food and Drug Administration, more than 1 million hernia repairs are performed in the United States alone. Common adverse events associated with hernia repair surgery include pain, infection, hernia recurrence, adhesion formation, obstruction, bleeding, and fluid build-up. Breast reconstruction may be performed to reconstruct a breast after a mastectomy has been performed to remove a diseased due to cancer or as a prophylactic measure to prevent cancer. Common adverse events associated with breast reconstruction include infection, pain, delayed healing, and swelling.

Thus there is a need for improved surgical repair materials and medical textiles.

SUMMARY OF THE DISCLOSURE

Described herein are surgical grafts and medical textiles having a reservoir of a desired agent that may be stored in and/or released from the surgical graft or medical textile that may be especially useful in diagnosing, imaging, managing, preventing or treating a condition, disease, disorder or other health or hygiene issue. Such surgical grafts and medical textiles may be useful for soft tissue reconstruction, regeneration, or repair. Such surgical grafts and medical textiles may be implantable or non-implantable. A surgical implant or medical textile may provide an internal source of a desired agent (e.g., an active agent such as an active pharmaceutical agent) to a patient. A desired agent may provide a diagnostic function, an imaging function, a therapeutic function or so forth. A desired agent may act to improve healing or manage pain. In some cases, a desired agent may be released from the surgical implant or medical textile over time (be time-release). A desired agent may act locally or may move through the body such as through the blood or lymph, and act systemically.

A surgical repair graft may include one or a plurality of stacked biotextile layers and a bioabsorbable carrier matrix attached to at least one of the biotextile layers and having a plurality of particles configured to release an active agent over an extended period of time (e.g., time release). The particles may have a biodegradable portion configured to biodegrade or reorganize over time and release an active agent from the particle. In some examples, the particles may not biodegrade or may release an active agent through a different process, such as diffusion through a membrane. Carrier matrix particles may include for example, cyclodextrins, dendrimers, a gel, gold, liposomes, micelles, multivesicular liposomes, microspheres, nanoparticles, proliposomes, quantum dots or the like. The particles may have a plurality of non-concentric internally aqueous chambers, each chamber surrounded by a lipid membrane, at least one of the lipid membrane and the aqueous chamber containing a desired agent.

One aspect of the invention provides a surgical repair graft including a plurality of stacked biotextile layers; and a bioabsorbable carrier matrix including multivesicular liposomes attached to at least one of the biotextile layers, the multivesicular liposomes including an active agent. Another aspect of the invention provides a surgical repair graft including a biotextile layer; and a bioabsorbable carrier matrix including multivesicular liposomes attached to the biotextile layer, the multivesicular liposomes including an active agent. Yet another aspect of the invention provides a surgical repair graft including a plurality of stacked biotextile layers; and a bioabsorbable carrier matrix including multivesicular liposomes attached to at least one of the biotextile layers, the multivesicular liposomes including an active agent, wherein the multivesicular liposomes include a plurality of particles each having a plurality of non-concentric internally aqueous chambers each surrounded by a lipid membrane, at least one of the aqueous chambers and the lipid membrane containing an active agent.

In some such surgical repair grafts the internally aqueous chambers may include the active agent. In some such surgical repair grafts the lipid membrane may include the active agent.

In some such surgical repair grafts the carrier matrix attached to the biotextile layer may be discontinuous and in some it may be continuous. In some such surgical repair grafts the carrier matrix may be attached to the biotextile layer at a plurality of discrete attachment sites. In some such surgical repair grafts the carrier matrix may be attached to the biotextile layer at a plurality of discrete attachment sites in a fixed pattern. In some such surgical repair grafts the carrier matrix may be attached to the biotextile layer in a random pattern or may be attached a fixed pattern (such as in an array).

In some such surgical repair grafts the carrier matrix may include a covering. In some such surgical repair grafts the carrier matrix may include a covering having a plurality of openings. In some such surgical repair grafts the carrier matrix may include a porous covering having a porosity of at least 100 pores per square inch (PPI). In some such surgical repair grafts the carrier matrix may include a porous covering having a porosity of between 10 pores per square inch (PPI) and 100 pores per square inch. In some such surgical repair grafts the biotextile layer may have a porosity of at least 100 pores per square inch (PPI). In some such surgical repair grafts the biotextile layer may have a porosity of between 10 pores per square inch (PPI) and 100 pores per square inch. In any of these surgical repair grafts at least one biotextile layer may have an open cell pore of between 0.5 mm and 6 mm diameter.

In some such surgical repair grafts the multivesicular liposomes may be generally spherically shaped. In some such surgical repair grafts the multivesicular liposomes may be generally smaller at an end opposite an attachment end than at an attachment end wherein the multivesicular liposomes are attached to the biotextile layer at the attachment end.

Some of these surgical repair grafts may further include one or more compliance control stitches. Some of these surgical repair grafts may further include patterns sewn or embroidered into the graft. Some of these surgical repair grafts may further include one or more compliance control stitch patterns including monofilament thread or yarns including polyethylene or polypropylene sewn or embroidered into the graft.

Some of these surgical repair grafts may further include one or more compliance control stitch patterns sewn or embroidered into the graft wherein the compliance strain of the biotextile layer is between 10-30% at 16 N/cm.

In some of these surgical repair grafts the multivesicular liposomes may include lipid bilayers. In some of these surgical repair grafts the multivesicular liposomes may include phospholipid bilayers. In some of these surgical repair grafts the multivesicular liposomes may include a lipid bilayer including phospholipid, cholesterol, and triglycerides. In some of these surgical repair grafts the multivesicular liposomes may include a lipid component including at least one amphipathic lipid and at least one neutral lipid lacking a hydrophilic head group. In some of these surgical repair grafts the multivesicular liposomes may include a lipid component including at least one amphipathic lipid, at least one neutral lipid lacking a hydrophilic head group, and a cholesterol and/or a plant sterol. In some of these surgical repair grafts the multivesicular liposomes may include lipid membranes, the lipid membranes charged on an outer surface of the multivesicular liposomes. In some of these surgical repair grafts the multivesicular liposomes may be from 1% (w/w) to 10% (w/w) lipid (or anything in between these amounts). In some of these surgical repair grafts the multivesicular liposomes may be between 10% (w/w) and 20% (w/w) lipid (or anything in between these amounts). In some of these surgical repair grafts the multivesicular liposomes may be from 80% (w/w) to 99% (w/w) aqueous (or anything in between these amounts). In some of these surgical repair grafts the multivesicular liposomes may be between 1 um and 500 um in a longest dimension (or anything in between these values). In some of these surgical repair grafts the multivesicular liposomes may be between 10 um and 50 um in a longest dimension (or anything in between these values). In some of these surgical repair grafts the multivesicular liposomes may be between 10 um and 50 um in diameter (or anything in between these values).

In some of these surgical repair grafts the multivesicular liposomes may include at least 2 internally aqueous chambers. In some of these surgical repair grafts the multivesicular liposomes may include at least 10 internally aqueous chambers. In some of these surgical repair grafts the multivesicular liposomes may include at least 100 internally aqueous chambers. In some of these surgical repair grafts the multivesicular liposomes may include at least 500 internally aqueous chambers. In some of these surgical repair grafts the multivesicular liposomes may include between 20 and 100 internally aqueous chambers.

In some of these surgical repair grafts at least one biotextile layer may include extracellular matrix, which may be naturally occurring or may be synthetic. In some of these surgical repair grafts at least one biotextile layer may include collagen. In some of these surgical repair grafts the carrier matrix may be between two of the biotextile layers.

In some of these surgical repair grafts the active agent may include an active pharmaceutical ingredient (API). In some of these surgical repair grafts the active agent may include an antifungal agent, antineoplastic agent, or an antibiotic. In some of these surgical repair grafts an active agent may include an analgesic. In some of these surgical repair grafts an active agent may include bupivacaine or bupivacaine phosphate.

In some of these surgical repair grafts the carrier matrix may be configured to release 50% of the active agent over a period of one day upon continuous exposure of the carrier matrix to a bodily fluid. In any of these surgical repair grafts the carrier matrix may be configured to release 90% of the active agent over a period of one day upon continuous exposure to a bodily fluid. In some of these surgical repair grafts the carrier matrix may be configured to release 50% of the active agent over a period of fourteen days upon continuous exposure to a bodily fluid. In some of these surgical repair grafts the carrier matrix may be configured to release 90% of the active agent over a period of fourteen days upon continuous exposure to a bodily fluid.

In some of these surgical repair grafts the carrier matrix or multivesicular liposomes may include internally aqueous chambers including or containing the active agent which may be dispersed, dissolved, encapsulated or otherwise held in the internally aqueous chambers. In some of these surgical repair grafts the carrier matrix or multivesicular liposomes may include a lipid membrane including or holding the active agent which may be embedded or otherwise held in the lipid membrane.

In some of these surgical repair grafts the carrier matrix may be configured to release 50% of the active agent over a period of one day upon continuous exposure to a bodily fluid. In some of these surgical repair grafts the carrier matrix may be configured to release 90% of the active agent over a period of one day upon continuous exposure to a bodily fluid. In some of these surgical repair grafts the carrier matrix may be configured to release 50% of the active agent over a period of fourteen days upon continuous exposure to a bodily fluid. In some of these surgical repair grafts the carrier matrix may be configured to release 90% of the active agent over a period of fourteen days upon continuous exposure to a bodily fluid. In some of these surgical repair grafts the carrier matrix may be at least 50% degraded within one day upon continuous exposure to a bodily fluid. In some of these surgical repair grafts the carrier matrix may be at least 50% degraded within 14 days upon continuous exposure to a bodily fluid. In some of these surgical repair grafts the carrier matrix may be at least 95% degraded within one day upon continuous exposure to a bodily fluid. In some of these surgical repair grafts the carrier matrix may be less than 95% degraded before one day and at least 95% degraded between 1 day and 5 days upon continuous exposure to a bodily fluid. In some of these surgical repair grafts the carrier matrix may be less than 95% degraded before 5 days and at least 95% degraded between 5 days and 14 days upon continuous exposure to a bodily fluid. In some of these surgical repair grafts the carrier matrix may be less than 95% degraded before 14 days and at least 95% degraded between 14 days and 45 days upon continuous exposure to a bodily fluid. In some of these surgical repair grafts the carrier matrix may be between 25% and 75% degraded within 7 days upon continuous exposure to a bodily fluid. In some of these surgical repair grafts the carrier matrix may be between 25% and 75% degraded between 7 days and 14 days upon continuous exposure to a bodily fluid.

In some of these surgical repair grafts may further include an adhesive adhering the carrier matrix to the biotextile layer. In some of these surgical repair grafts may further include a polymer between the carrier matrix and the biotextile layer, the polymer adhering the carrier matrix to the biotextile layer. In some of these surgical repair grafts may further include a hydrogel between the carrier matrix and the biotextile layer, the hydrogel adhering the carrier matrix to the biotextile layer. In some of these surgical repair grafts may further include a hydrogel between the carrier matrix (or multivesicular liposomes) and the biotextile layer, the hydrogel adhering the carrier matrix (or multivesicular liposomes) to the biotextile layer wherein the hydrogel is chemically bonded to the carrier matrix (or multivesicular liposomes). Some of these surgical repair grafts may further include a hydrogel between the carrier matrix and the biotextile layer, the hydrogel adhering the carrier matrix to the biotextile layer wherein the hydrogel is non-covalently chemically bonded to the multivesicular liposomes. Some of these surgical repair grafts may further include a hydrogel between the carrier matrix (or multivesicular liposomes) and the biotextile layer, the hydrogel adhering the carrier matrix (or multivesicular liposomes) to the biotextile layer wherein the hydrogel is covalently chemically bonded to the carrier matrix (or multivesicular liposomes). Some of these surgical repair grafts may further include a polymer such as alginate, cellulose, chitosan, collagen, polyhydroxyacid, derivatized cellulose, gelatin, polyanhydrides, polycaprolactone, polyhydroxy acid, polyglycolic acid, polylactic acid, or polyorthoester between the carrier matrix and the biotextile layer, the polymer adhering the carrier matrix to the biotextile layer. Some of these surgical repair grafts may further include a cross-linked polymeric hydrogel between the carrier matrix and the biotextile layer, the polymeric hydrogel adhering the carrier matrix to the biotextile layer, the cross-link derived from acrylamide, allyl methacrylate, dimethacrylate, dimethyl suberimidate, DMS-treated collagen, dimethyl 3, 3'-dithiobispropionimidate, ethylene glycol, glutaraldehyde, N, N methylene-bisacrylamide, transglutaminase, or tripolyphosphate.

In some of these surgical repair grafts, a second of the biotextile layers may be flexibly attached to a first of the biotextile layers with a pattern of discrete attachment sites having a density of attachment sites that is less than about 10 attachments/mm$^2$. In some of these surgical repair grafts, a second of the biotextile layers may be flexibly attached to a first of the biotextile layers with a pattern of discrete attachment sites having a density of attachment sites between 10 attachment sites/mm$^2$ and 100 attachment sites/mm$^2$. In some of these surgical repair grafts, a biotextile layer may have a pattern of reinforced discrete compliance control sites having a density of sites that may be fewer than about 10 attachments/mm$^2$. In any of these surgical repair grafts, a biotextile layer may have a pattern of reinforced discrete compliance control sites having a density of sites that may be between 10 attachments/mm$^2$ and 100 attachments/mm$^2$.

In some of these surgical repair grafts a compliance of the surgical repair graft may be less than 15% different from a compliance of a similar surgical repair graft lacking the carrier matrix.

In some of these surgical repair grafts a compliance of the surgical repair graft may increase over time when the carrier matrix is exposed to an aqueous solution. In some of these surgical repair grafts a compliance of the surgical repair graft may increase over time when the carrier matrix is exposed to an aqueous solution and the biotextile layer or plurality of stacked biotextile layers remain intact. In some of these surgical repair grafts a compliance of the surgical repair graft may increase over time when the carrier matrix is exposed to a bodily fluid and the stacked layers remain intact. In any of these surgical repair grafts, a compliance of the surgical repair graft may change or increase by less than 1%, less than 5% or less than 10% when the carrier matrix is continuously exposed to a bodily fluid for 1 day, 1 week, 2 weeks, 4 weeks, 6 weeks, or 12 weeks. In some of these surgical repair grafts a compliance of the surgical repair graft may differ by less than 20% compared with the compliance of similarly stacked layers without carrier matrix when the grafts are continuously exposed to a bodily fluid for 12 weeks. In some of these surgical repair grafts a compliance of the surgical repair graft may differ by less than 5% compared with the compliance of similarly stacked layers without carrier matrix when the grafts are continuously exposed to a bodily fluid for 12 weeks. In some of these surgical repair grafts a difference in uniaxial tension of the surgical repair graft may change by less than 20% when the carrier matrix is adhered thereto compared with the uniaxial tension of a similar surgical repair without carrier matrix. In some of these surgical repair grafts a difference in uniaxial tension of the surgical repair may change by less than 5% when the carrier matrix is adhered thereto compared with the uniaxial tension of a similar surgical repair graft without carrier matrix. In some of these surgical repair grafts a difference in bending stiffness of the surgical repair graft may change by less than 20% when the carrier matrix is adhered thereto compared with the bending stiffness of a similar surgical repair graft without carrier matrix. In some of these surgical repair grafts a bending stiffness of the surgical repair graft may change by less than 5% when the carrier matrix is adhered thereto compared with the axial tensile modulus of a similar surgical repair graft without carrier matrix. In some of these surgical repair grafts a difference in burst strength of the surgical repair graft may change by less than 20% when the carrier matrix is adhered thereto compared with the burst strength of a similar surgical repair graft without carrier matrix. In some of these surgical repair grafts a difference in burst strength of the surgical repair graft may change by less than 5% when the carrier matrix is adhered thereto compared with the burst strength of a similar surgical repair graft without carrier matrix. In any of these surgical repair grafts a difference in surface roughness of the layers may change by less than 20% when the carrier matrix is adhered thereto compared with the burst strength of a similar surgical repair graft without carrier matrix. In some of these surgical repair grafts a difference in surface roughness of the layers may change by less than 20% when the carrier matrix is adhered thereto compared with the burst strength of a similar surgical repair graft without carrier matrix.

Another aspect of the invention includes a method for controlled release of an active agent from a surgical repair graft including the steps of exposing a surgical repair graft having one biotextile layer or a plurality of stacked biotextile layers and a bioabsorbable carrier matrix attached to the one or at least one of the plurality of stacked biotextile layers to an aqueous fluid, the carrier matrix including an active agent; and degrading the carrier matrix over time by the aqueous fluid to thereby release the active agent from the carrier matrix. Yet another aspect of the invention includes a method for controlled release of an active agent from a surgical repair graft including: exposing a surgical repair graft having one biotextile layer or a plurality of stacked biotextile layers and a bioabsorbable carrier matrix attached to at least one of the one or plurality of stacked biotextile layers to an aqueous fluid, the carrier matrix including an active agent; and degrading the carrier matrix over time by the aqueous fluid to thereby release the active agent from the carrier matrix, wherein the bioabsorbable carrier matrix includes multivesicular liposomes. Yet another aspect of the invention includes a method for controlled release of an active agent from a surgical repair graft including: exposing a surgical repair graft having one biotextile layer or a plurality of stacked biotextile layers and a bioabsorbable carrier matrix attached to at least one of the one or plurality of stacked biotextile layers to an aqueous fluid, the carrier matrix including an active agent; and degrading the carrier matrix over time by the aqueous fluid to thereby release the active agent from the carrier matrix wherein the bioabsorbable carrier matrix includes a plurality of particles each having a plurality non-concentric internally aqueous chambers surrounded by lipid membranes, one or more of the internally aqueous chambers and the lipid membranes containing the active agent.

In some of these methods the bioabsorbable carrier matrix may include a plurality of particles each having a plurality non-concentric internally aqueous chambers surrounded by lipid membranes, one or more of the internally aqueous chambers and the lipid membranes containing the active agent, wherein a first set of the chambers are on the exterior of the particles and a second set of chambers are on the interior of the particles, wherein lipid membranes on the first set of chambers are degraded first and lipid membranes on the second set of chambers are degraded later during the degrading step.

In some of these methods the one biotextile layer or at least one of the plurality of biotextile layers may include pores, the method further including flowing active agent from the carrier matrix through the pores to thereby release active agent to a body region adjacent the biotextile layer.

In some of these methods a hydrogel may be adhered to at least one of the layers, the method further including degrading the hydrogel. In some of these methods a hydrogel may be adhered to at least one of the layers wherein the hydrogel remains adhered after at least 50% or at least 95% of the active agent has been released.

In some of these methods the aqueous fluid may include a bodily fluid. In some of these methods an aqueous fluid may include blood, lactation fluid, interstitial fluid, lymph fluid, menstrual fluid or wound exudate fluid.

In some of these methods a compliance strain of the surgical repair graft may be between 10-30% at 16 N/cm prior to the degrading step. In some of these methods the compliance strain of the surgical repair graft is between 10-30% at 16 N/cm 90 days after the beginning of the degrading step. In some of these methods the compliance strain of the surgical repair graft may be between 10-30% at 16 N/cm both before and 15 days after the beginning of the degrading step.

In some of these methods the carrier matrix may be between 1% (w/w) and 10% (w/w) lipid or from 10% (w/w) to 20% (w/w) lipid prior to the degrading step (or anything in between these values). In some of these methods the carrier matrix may be between 80% (w/w) and 99% (w/w) aqueous prior to the degrading step (or anything in between these values).

In some of these methods the particles may include at least 10 internally aqueous chambers prior to the exposing step. In some of these methods the particles may include at least 10 internally aqueous chambers 1 day after the beginning of the exposing step. In some of these methods the particles may include at least 10 internally aqueous chambers 14 days after the beginning of the exposing step. In some of these methods the particles may include at least 50 internally aqueous chambers prior to the exposing step. In some of these methods the particles may include at least 50 internally aqueous chambers 1 day after the beginning of the exposing step. In some of these methods the particles may include at least 50 internally aqueous chambers 14 days after the beginning of the exposing step. In some of these methods the particles may include between 20 and 100 internally aqueous chambers or from 100 to 100 internally aqueous chambers prior to the exposing step (or anything in between these values).

In some of these methods the active agent may include an active pharmaceutical ingredient (API). In some of these methods the active agent may include an antifungal agent, an antineoplastic agent, or an antibiotic. In some of these methods the active agent may include a pain medication.

In some of these methods the internally aqueous chambers may contain the active agent. In some of these methods the active agent may be embedded or otherwise held in the lipid membrane.

In some of these methods the carrier matrix may be at least 50% degraded within one day after the beginning of the exposing step with continuous exposure to the aqueous fluid. In some of these methods the carrier matrix may be at least 50% degraded between one day and fourteen days after the beginning of the exposing step with continuous exposure to the aqueous fluid. In some of these methods the carrier matrix may be at least 50% degraded between fourteen days and ninety days after the beginning of the exposing step with continuous exposure to the aqueous fluid. In some of these methods the carrier matrix may be at least 95% degraded within one day after the beginning of the exposing step with continuous exposure to the aqueous fluid. In some of these methods the carrier matrix may be at least 95% degraded between one day and fourteen days after the beginning of the exposing step with continuous exposure to the aqueous fluid. In some of these methods the carrier matrix may be at least 95% degraded between fourteen days and ninety days after the beginning of the exposing step with continuous exposure to the aqueous fluid.

In some of these methods the carrier matrix may be between 25% and 75% degraded between one day and fourteen days after the beginning of the exposing step with continuous exposure to the aqueous fluid. In some of these methods the carrier matrix is between 25% and 75% degraded between fourteen days and ninety days after the beginning of the exposing step with continuous exposure to the aqueous fluid.

Some of these methods may further include an adhesive adhering the carrier matrix to the biotextile layer. Some of these methods may further include a hydrogel adhering the carrier matrix to the biotextile layer. Some of these methods may further include a hydrogel adhering the lipid membrane to the biotextile layer. Some of these methods may further include a hydrogel adhering the carrier matrix to the biotextile layer wherein the hydrogel is chemically bonded to the carrier matrix. Some of these methods may further include a hydrogel adhering the carrier matrix to the biotextile layer wherein the hydrogel is chemically bonded to the carrier matrix through chemical bonds, wherein the method further includes breaking the chemical bonds.

Some of these methods may further include a hydrogel adhering the carrier matrix to the biotextile layer wherein the hydrogel is non-covalently chemically bonded to the carrier matrix. Some of these methods may further include a hydrogel adhering the carrier matrix to the biotextile layer wherein the hydrogel is covalently chemically bonded to the carrier matrix. Some of these methods may further include a polymeric hydrogel between the carrier matrix and the biotextile layer adhering the carrier to the biotextile layer, the polymeric hydrogel including alginate, cellulose, chitosan, collagen, polyhydroxyacids, derivatized cellulose, gelatin, polyanhydrides, polycaprolactone, polyhydroxy acids, polyglycolic acid, polylactic acid, or polyorthoester. Some of these methods may further include a cross-linked polymeric hydrogel between the carrier matrix and the biotextile layer adhering the carrier to the biotextile layer, the cross-link derived from acrylamide, allyl methacrylate, dimethacrylate, dimethyl suberimidate, DMS-treated collagen, dimethyl 3, 3'-dithiobispropionimidate, ethylene glycol, glutaraldehyde, N, N methylene-bisacrylamide, transglutaminase, or tripolyphosphate.

Some of these methods may further include a second of the biotextile layers flexibly attached to a first of the biotextile layers with a pattern of discrete attachment sites having a density of attachment sites that is fewer than 10 attachments/mm$^2$ and the number of attachment sites is substantially unchanged 30 days after the beginning of the degrading step. In some of these methods a second of the biotextile layers may be flexibly attached to a first of the biotextile layers with a pattern of discrete attachment sites having a density of attachment sites between 10 attachments/mm$^2$ and 100 attachment sites prior to the exposing step. In some of these methods a second of the biotextile layers may be flexibly attached to a first of the biotextile layers with a pattern of discrete attachment sites having a density of attachment sites between 10 attachments/mm$^2$ and 100 attachment sites number of attachment sites is substantially unchanged 30 days after the beginning of the degrading step.

In some of these methods a compliance of the surgical repair graft may change up to 20% 14 days after the beginning of the degrading step. In some of these methods a compliance of the surgical repair graft may change by less than 5% 14 days after the beginning of the degrading step. In some of these methods a uniaxial tension of the surgical repair graft may change up to 20% 14 days after the beginning of the degrading step. In some of these methods a uniaxial tension of the surgical repair graft may change by less than 5% 14 days after the beginning of the degrading step. In some of these methods a bending stiffness of the surgical repair graft may change up to 20% 14 days after the beginning of the degrading step. In some of these methods a bending stiffness of the surgical repair graft may change by less than 5% 14 days after the beginning of the degrading step. In some of these methods a burst strength of the surgical repair graft may change from 5% to 20% 14 days after the beginning of the degrading step. In some of these methods a burst strength of the surgical repair graft may change by less than 5% 14 days after the beginning of the degrading step. In some of these methods a roughness of the surgical repair graft may change up from 5% to 20% 14 days after the beginning of the degrading step. In some of these methods a roughness of the surgical repair graft may change by less than 5% 14 days after the beginning of the degrading step.

Yet another aspect of the invention provides a method for manufacturing a surgical repair graft including: hydrating a biotextile layer; and adhering to the biotextile layer a carrier matrix including multivesicular liposomes to thereby form a surgical repair graft. Yet another aspect of the invention provides a method for manufacturing a surgical repair graft including: hydrating a biotextile layer; and adhering to the biotextile layer a carrier matrix including a plurality of particles having non-concentric internally aqueous chambers containing a lipid-encapsulated drug to create an attached biotextile layer to thereby form a surgical repair graft.

In some of these methods a compliance of the surgical repair graft may differ by 10% to less than 20% from a similar surgical repair graft without the multivesicular liposomes or plurality of particles. In some of these methods a compliance of the surgical repair graft may differ by 5% to less than 10% from a similar surgical repair graft without the multivesicular liposomes or plurality of particles. In some of these methods a compliance of the surgical repair graft may differ by less than 5% from a similar surgical repair graft without the multivesicular liposomes or plurality of particles. In some of these methods a compliance of the surgical repair graft may differ by less than 1% from a similar surgical repair graft without the multivesicular liposomes or plurality of particles. In some of these methods the biotextile layer may include collagen.

Some of these methods may further include the step of adhering a hydrogel to the biotextile layer and to the carrier matrix such that the hydrogel is between the biotextile layer and the carrier matrix. Some of these methods may further include the step of adhering a hydrogel to the biotextile layer and to the carrier matrix such that the hydrogel is between the biotextile layer and the carrier matrix wherein a compliance of the surgical repair graft differs by less than 20% or less than 10% from a similar surgical repair graft without the multivesicular liposomes or plurality of particles or hydrogel.

Some of these methods may further may include the step of adhering a hydrogel to the biotextile layer and to the carrier matrix such that the hydrogel is between the biotextile layer and the carrier matrix wherein a bending stiffness of the surgical repair graft differs by less than 20% from a similar surgical repair graft without the multivesicular liposomes or plurality of particles or hydrogel. Some of these methods may further include the step of swelling a hydrogel in an aqueous solution and adhering the hydrogel to the biotextile layer and to the carrier matrix such that the hydrogel is between the biotextile layer and the carrier matrix wherein a bending stiffness of the surgical repair graft differs by less than 20% from a similar surgical repair graft without the multivesicular liposomes or plurality of particles or hydrogel. Some of these methods may include the step of cross-linking the hydrogel. Some of these methods may include the step of attaching (covalently or non-covalently) the hydrogel to the carrier matrix. Some of these steps may include of attaching (covalently or non-covalently) amino acids in the hydrogel to amino acids in the carrier matrix.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1A shows the surgical repair graft without added tension. FIG. 1B shows the surgical repair graft of FIG. 1A when the graft is axially stretched. FIG. 1C shows the surgical repair graft of FIG. 1A when the graft is bent.

FIG. 1D shows the surgical repair graft with the coating without added tension. FIG. 1E shows the surgical repair graft of FIG. 1D when the graft is axially stretched. FIG. 1F shows the surgical repair graft of FIG. 1A when the graft is bent.

FIG. 2A, FIG. 2B, and FIG. 2C show another surgical repair graft with a plurality of attached carrier particles shaped to allow the graft to stretch and bend. FIG. 2A shows the surgical repair graft without added tension. FIG. 2B shows the surgical repair graft of FIG. 2A when the graft is axially stretched.

FIG. 4A, FIG. 4B, and FIG. 4C show side views of another surgical repair graft with a plurality of block shaped carrier matrix particles attached. FIG. 4A shows the surgical repair graft without added tension. FIG. 4B shows the surgical repair graft of FIG. 4A when the graft is axially stretched. FIG. 4C shows the surgical repair graft of FIG. 4A when the graft is bent.

FIG. 5A, FIG. 5B, and FIG. 5C show side views of another surgical repair graft with a plurality of attached soft shell carrier matrix particles. FIG. 5A shows the surgical repair graft without added tension. FIG. 5B shows the surgical repair graft of FIG. 5A when the graft is axially stretched. FIG. 5C shows the surgical repair graft of FIG. 5A when the graft is bent.

FIG. 6A, FIG. 6B, and FIG. 6C show side views of another surgical repair graft with a plurality of very short block shaped carrier matrix particles attached. FIG. 6A shows the surgical repair graft without added tension. FIG. 6B shows the surgical repair graft of FIG. 6A when the graft is axially stretched. FIG. 6C shows the surgical repair graft of FIG. 6A when the graft is bent.

FIG. 6D, FIG. 6E, and FIG. 6F show side views of a surgical repair graft with a plurality of relatively tall block shaped carrier matrix particles attached. FIG. 6D shows the surgical repair graft without added tension. FIG. 6E shows the surgical repair graft of FIG. 6D when the graft is axially stretched. FIG. 6F shows the surgical repair graft of FIG. 6D when the graft is bent.

FIG. 7A and FIG. 7B show views of another surgical repair graft having a relatively homogenous carrier matrix coating. FIG. 7A shows the repair graft without added tension. FIG. 7B shows the repair graft from FIG. 7B under added tension.

FIG. 7C and FIG. 7D show views of another surgical repair graft having a relatively homogenous carrier matrix coating with slits or openings in the coating. FIG. 7C shows the repair graft without added tension. FIG. 7D shows the repair graft under added tension; the slits or openings open and allow the coating (and graft) to stretch and bend.

FIG. 8A, FIG. 8B, and FIG. 8C show side views of another surgical repair graft with a carrier matrix attached through an adhesive intermediate. FIG. 8A shows the surgical repair graft at rest without added tension. FIG. 8B shows the surgical repair graft of FIG. 8A when the graft is axially stretched. FIG. 8C shows the surgical repair graft of FIG. 8A when the graft is bent.

FIG. 10A shows a carrier matrix particle having a plurality of non-concentric internally aqueous chambers each surrounded by a lipid membrane and containing different types of agents in different chambers. FIG. 10B shows a partially degraded version of the carrier matrix particle shown in FIG. 10A.

FIG. 11A shows a carrier matrix particle having a plurality of non-concentric internally aqueous chambers each surrounded by a lipid membrane and containing different types of agents in each chamber. FIG. 11B shows a partially degraded version of carrier matrix particle shown in FIG. 11A.

DETAILED DESCRIPTION

Described herein are surgical repair graft devices and medical textile devices configured to carry an agent (e.g., an active agent such as a drug) and methods of making and using such devices. Such a surgical repair graft may serve to release the agent over a period of time (be time-release). As used herein, a surgical repair graft (or medical textile) may refer to a device having one or more biotextile layers and a carrier matrix adhered to at least one layer, the graft configured for implanting into a body (e.g., a mammalian body). Such a surgical repair graft or medical textile may release an agent into the body (in vivo release) or external to or on the body. In general, the surgical repair graft or medical textile maintains advantageous mechanical properties (e.g., strength, flexibility, compliance, etc.) for use in soft tissue reconstruction, regeneration, or repair.

A surgical repair graft as described herein may be useful for supporting or repairing a body tissue such as for breast reconstruction, hernia repair, pelvic organ prolapse treatment, and so forth. In some examples it may be implanted or used to serve as a source of a desired agent.

In some embodiments, the surgical repair graft includes one layer or a plurality of stacked layers (e.g., a plurality of stacked biotextile layers), and a bioabsorbable carrier matrix including a multivesicular liposome attached to one or more than one biotextile layers, the multivesicular liposome including an active agent. In some particular examples, the carrier matrix has a plurality of particles each having a plurality of non-concentric internally aqueous chambers each surrounded by a lipid membrane, wherein at least one or more of the lipid membrane and the aqueous chamber contain an active agent. As used herein, a description of a surgical repair graft may also apply to a medical textile, such as one used for eye treatment, sutures, wound dressing, and so on.

Figure 1:
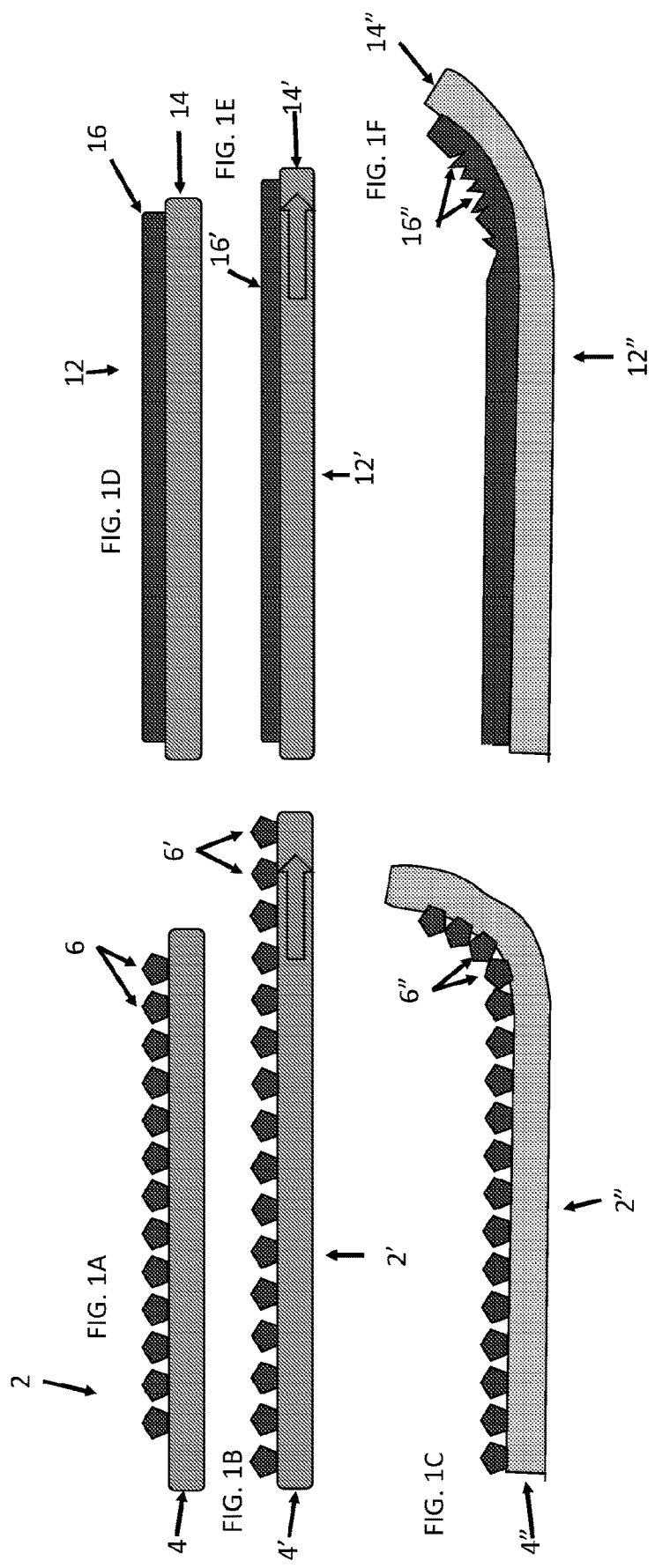
FIG. 1A, FIG. 1B, and FIG. 1C show a surgical repair graft as described herein having a plurality of attached carrier particles.
FIG. 1D, FIG. 1E, and FIG. 1F show a surgical repair graft with a coating or film that reduces axial compliance and increases bending stiffness.

FIG. 1A, FIG. 1B, and FIG. 1C show an example of a surgical repair graft with a plurality of attached carrier particles, the surgical repair graft having one or more biotextile layers and a carrier matrix adhered to at least one layer, the graft configured for implanting into a body (e.g., an animal or mammalian body).

A layer or layers of a surgical repair graft as described herein generally have biomechanical properties that match or are similar to the biomechanical properties of the tissues they are replacing or repairing. Such biomechanical properties of a surgical implant may be described, for example by bending stiffness, compliance, elasticity, uniaxial tension, burst strength, roughness, and so on.

A surgical repair graft may be made of any materials or combination of materials that alone or in combination supply desired mechanical properties and other desired characteristics such as biocompatibility and biostability. A graft may serve as a time-release depot for agent (e.g., active agent such as a drug) release. A graft may include multiple components such as one or more biotextile layer(s); a carrier matrix containing an agent; an adhesive that adheres carrier matrix to a biotextile layer, etc.). A component may be made from naturally occurring materials and/or from synthetic materials.

In some examples, a biotextile layer(s) of a surgical repair graft may be made from extracellular matrix (ECM) and/or may be synthesized to mimic the properties of extracellular matrix. In some examples, a biotextile layer may be made from or may include naturally occurring or synthetic extracellular matrix materials such as collagen, elastin, fibronectin, INTERGARD™, laminin, TIGR®, ULTRAPRO™ and so on. In some examples, a biotextile layer (or adhesive) is made from a naturally occurring collagen such as avian collagen, bovine collagen, fish collagen, marine animal collagen, ovine collagen, or porcine collagen. A collagen or other naturally occurring material may be harvested from any source, such as an organ or part of an organ, such as dermis, forestomach, intestine, pericardium, peritoneum, rumen (stomach), skin, stomach, tail, etc. of any organism. In other examples, collagen or another graft component may be manufactured by recombinant or other synthetic processes.

A carrier matrix as used herein includes a plurality of particles configured to carry and hold an agent for use in (or on) the body. In general, an agent in a carrier matrix is an active agent configured for release into the body to have an effect in the body and a carrier matrix is at least partially biodegradable to release the active agent into the body, but this is not necessarily the case. For example, a carrier matrix may hold a fluoroscopic agent for use for imaging purposes and the carrier matrix or part of a carrier matrix may not degrade and the fluoroscopic agent may remain in the carrier matrix. In some embodiments, a carrier matrix attached to a biotextile layer is discontinuous. FIG. 1A, FIG. 1B, and FIG. 1C show the same surgical graft under different conditions. FIG. 1A shows surgical repair graft 2 in an unstretched state. Carrier matrix particles 6 are attached to substrate or biotextile layer 4. FIG. 1B shows the same graft shown in FIG. 1A that has been subject to a stretching force (shown by the arrow). FIG. 1C shows the same surgical repair graft 2' that has been subject to a bending force. Due to the space between particles 6', the region of substrate 4' between particles 6' is able to stretch (or compress) and thus allow surgical graft 2' to stretch with little or no change to stretchability or relative to a similar surgical graft lacking such particles. Additionally as shown in FIG. 1C, substrate 4" is sufficiently flexible to bend and the space between particles 6" and the shape of particles 6" allows room for particles 6" to not interfere with each other as the graft bends and folds towards itself. By comparison, FIG. 1D, FIG. 1E, and FIG. 1F show a surgical repair graft with a covering (e.g., a coating or sheet) that limits axial compliance and increases bending stiffness compared with a similar surgical repair graft without a covering. FIG. 1D shows surgical repair graft 12 with covering 16 on substrate 14 in an unstressed state. FIG. 1E shows the same surgical repair graft 12' as the one shown in FIG. 1A that has been subject to a stretching force (shown by the arrow). Although some stretching takes place, coating 16' limits the ability of substrate 14' to stretch. FIG. 1F shows the same surgical repair graft 14" as shown in FIG. 1D and FIG. 1E that has been subject to a bending force. Coating 16" deforms and wrinkles when bent and prevents substrate 14" from bending too far. Because the covering resists an applied axial force and wrinkles on bending, the surgical grafts in FIG. 1E and FIG. 1F resist stretching and bending. Bending of such a relatively noncompliant graft may also result in such as wrinkling or separation of the covering from the biotextile.

Figure 2:
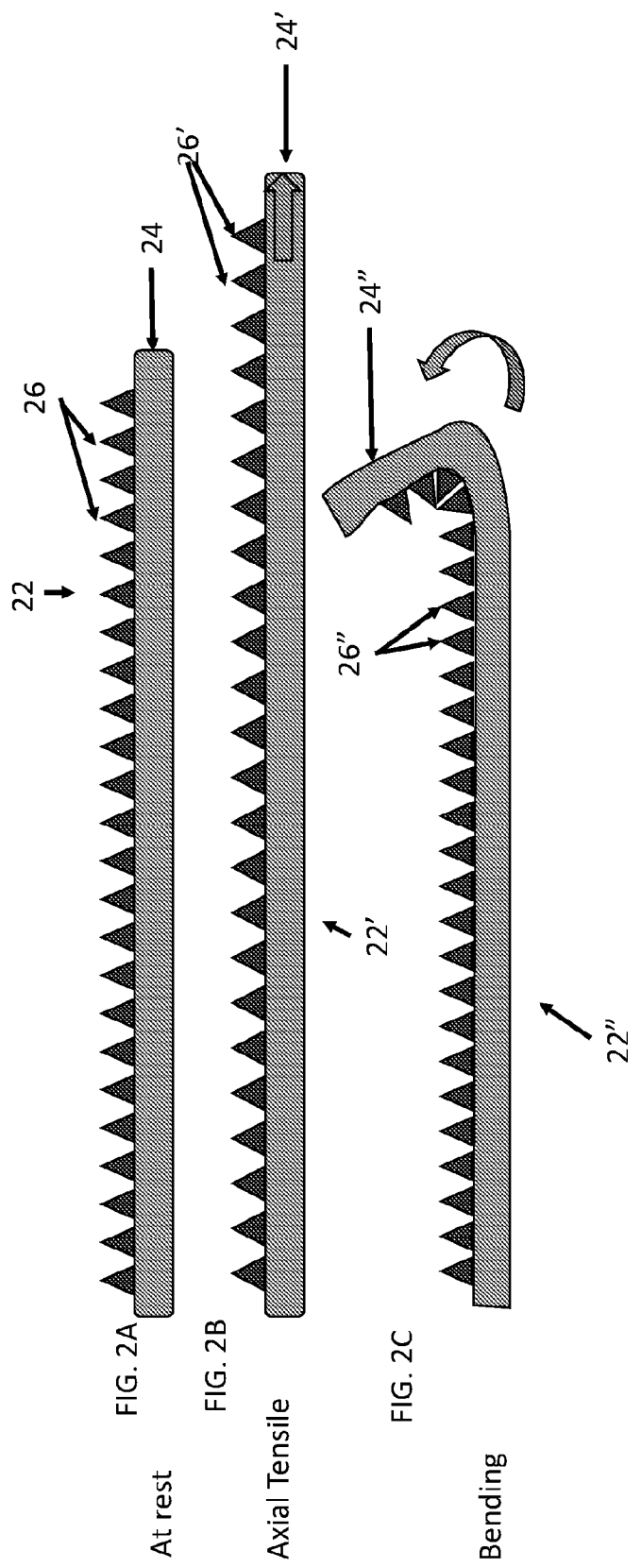
FIG. 2 shows the surgical repair graft of FIG. 2A when the graft is bent.
Figure 3:
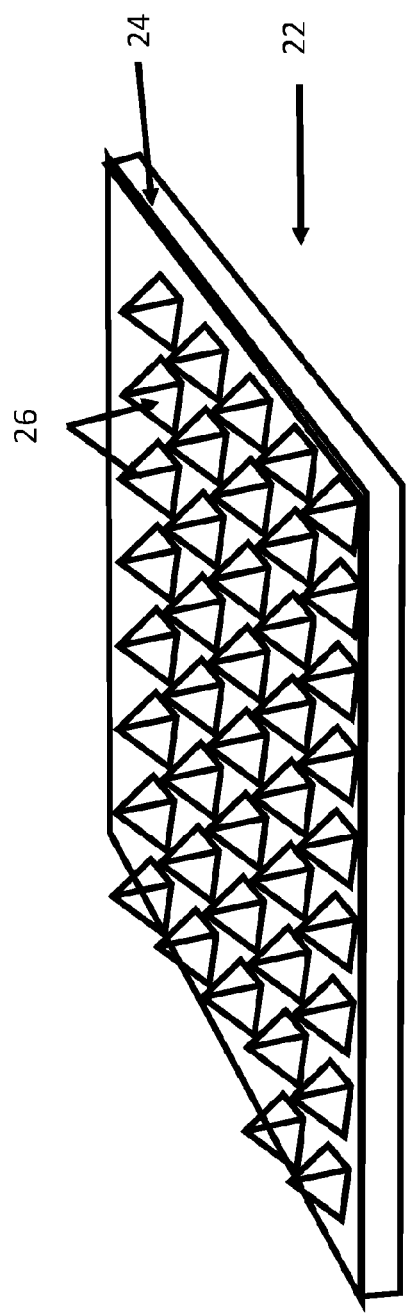
FIG. 3 shows another view of a surgical repair graft with a plurality of pyramidally shaped carrier matrix particles attached to a biotextile layer.

Carrier matrix particles can be any shape and can be regularly shaped or irregularly shaped. In some examples, a carrier matrix (e.g., of a surgical graft) includes particles that are generally block-shaped, conical, cuboidal, cylindrical, ellipsoidal, helical, pyramidal, spherical, square pyramidal, rectangular prism shaped, rectangular pyramidal, or tetrahedral, etc. and a carrier matrix may include one or more than one different shapes of particles. In some examples, a swath of a textile may have one shape of carrier matrix particles while another swath may have another shape. This may for example be useful to provide a graft that is relatively more compliant or more bendable in a first portion and less compliant or less bendable in a second portion. In some examples, a swath of a textile or an entire textile may have a mixture of different shapes of particles. Such a mixture may be regular or irregular (random). FIG. 2A, FIG. 2B, and FIG. 2C show a side view of a surgical repair graft with a plurality of pyramidal shaped carrier particles attached to a biotextile layer at rest and under different types of tension and FIG. 3 shows a perspective view. FIG. 2A and FIG. 3 show surgical repair graft 22 at rest without added tension on the graft. FIG. 2B shows surgical repair graft of FIG. 2A in which surgical repair graft 22' is axially stretched and FIG. 2C shows the surgical repair graft of FIG. 2A when surgical repair graft 22" is bent. FIG. 2A, FIG. 2B, and FIG. 2C and FIG. 3 show carrier particles attached to the biotextile layer at an attachment end and unattached to the biotextile layer at an unattached end. FIG. 2A, FIG. 2B, and FIG. 2C show carrier matrix particles larger at an attachment end whereby they are attached (either directly or through an intermediate component such as an adhesive) to a biotextile layer and smaller at an unattached end whereby they are unattached to the biotextile layer. In FIGS. 2A and 3, pyramidal shaped carrier matrix particles 26 are attached to layer 24 of surgical graft 22. In FIG. 2B, as a stretching tension shown by the arrow in FIG. 2B is applied to graft 24' to axially stretch layer 22', sections of layer 22' in between attached particles 26' (particle "nodes") are free to stretch in response to the stretching, allowing the biotextile layer (and graft as a whole) to readily stretch. In some examples, axial compliance of the graft having the carrier matrix attached to the substrate may be not significantly different (e.g., between 0% and 30% different or anything in between such as between 5% and 10%) from axial compliance of a similar graft that does not have the carrier matrix attached. In FIG. 2C, as a force shown by the arrow is applied to graft 22" to bend graft 22", sections of layer 22' between attached particles 26' (particle "nodes") are able to compress and bend and the opposing side of layer 22" away from the particles is free to stretch, and the graft is free to bend. In some examples, bend resistance of the graft having the carrier matrix attached may be or may be not significantly different (e.g., between 0% and 30% different or anything in between such as between 5% and 10%) from bend resistance of a similar graft that does not have carrier matrix attached. Additionally, since attached particles 26" are narrower towards their unattached end than at their attached end, attached particles 26" do not bump into each other when graft 22" bends and graft 22" is able to bend without undue interference from attached particles 26". Having a larger attached end may be beneficial for providing space to carry an agent (an active agent) into a body.

FIG. 4A, FIG. 4B, and FIG. 4C show side views of another surgical repair graft with a plurality of block shaped attached carrier matrix particles under different degrees of force, such as those that might be experienced in a patient's body. The particles may be for example cuboidal or rectangular prism shaped. FIG. 4A shows surgical repair graft 82 at rest without added tension. FIG. 4B shows surgical repair graft 84' when the graft is placed under axial tension and stretched. FIG. 4C shows surgical repair graft 84" of FIG. 4A when the graft is placed under a bending force. In FIG. 4A carrier matrix particles 86 are attached to layer 84. In FIG. 4B, as a stretching tension shown by the arrow is applied to graft 84' to axially stretch layer 82', sections of layer 82' in between attached particles 86' (particle "nodes") are free to stretch in response to the stretching. Axial compliance of the graft having the carrier matrix attached may be or maybe not significantly different (e.g., between 0% and 30% different or anything in between such as between 5% and 10%) from axial compliance of a similar graft that does not have the carrier matrix attached. However, in FIG. 4C, as a force shown by the arrow is applied to graft 82" to bend graft 82", bend resistance of the graft having the carrier matrix attached to it is ultimately increased compared with bend resistance of a similar graft that does not have carrier matrix attached. Sections of layer 82" in between attached particles 86" are able to squeeze together to a limited degree before carrier particles 86" begin to collide and restrict further bending (as shown by the free arrow). Graft 84 has an axial compliance that may be minimally affected by the attachment of particles 86, while bend resistance is increased. Particles 86 are relatively large and may carry a significant amount of active agent and graft 86 (or a portion of a graft 86) may be useful in an area where relatively more bending stiffness is acceptable or desired.

FIG. 5A, FIG. 5B, and FIG. 5C show side views of another surgical repair graft with a plurality of attached soft shell carrier particles at rest and under different types of tension. FIG. 5A shows surgical repair graft 102 at rest without added tension. FIG. 5B shows surgical repair graft 102' when the graft is axially stretched. FIG. 5C shows surgical repair graft 102" when the graft is bent. FIG. 5A shows surgical graft 102 with soft shell carrier particles 106 attached to biotextile layer 104. In FIG. 5B, as a stretching tension shown by the arrow is applied to graft 104' to axially stretch layer 102', sections of layer 102' in between attached particles 106' (particle "nodes") are free to stretch in response to the stretching. Axial compliance of the graft having the soft shell carrier matrix attached may be or may be not significantly different (e.g., between 0% and 30% different or anything in between such as between 5% and 10%) from axial compliance of a similar graft that does not have the carrier matrix attached. In FIG. 5C, as a force shown by the curved arrow is applied to surgical repair graft 102" to bend surgical repair graft 102", soft shell carrier particles 106" are pressed against one another. Soft shell carrier particles are sufficiently soft or pliable and are configured to deform in response to an applied force. In response to being pressed against one another, the particles readily morph, changing shape, indenting or deforming. Bend resistance of the graft having the soft shell carrier matrix attached may be or may not be significantly different (e.g., between 0% and 30% different or anything in between such as between 5% and 10%) from bend resistance of a similar graft that does not have the carrier matrix attached. Although particle morphing is illustrated as occurring when particles contact one another, particles may also or instead morph in response to contacting a biotextile layer, a body part, etc.

FIG. 6A, FIG. 6B, and FIG. 6C show side views of another surgical repair graft with a plurality of attached relatively short carrier particles at rest and under different types of tension. The particles may, for example, be cuboidal or rectangular. Although the particles may be similarly shaped to those of FIG. 4A, FIG. 4B, and FIG. 4C, they are shorter and grafts having them generally show less bending resistance. FIG. 6A shows surgical repair graft 122 at rest without added tension. FIG. 6B shows surgical repair graft 122' when the graft is placed under axial tension and axially stretched. FIG. 6C shows surgical repair graft 122" when the graft is placed under a bending tension and the graft is bent. In FIG. 6A, carrier matrix particles 126 are attached to biotextile layer 124 of surgical graft 122. In FIG. 6B, as a stretching tension in the direction shown by the large arrow in FIG. 6B is applied to graft 124' to axially stretch biotextile layer 122', sections of layer 122' in between attached particles 126' (particle "nodes") are free to stretch in response to the stretching. Axial compliance of the graft having the relatively short carrier matrix particles attached may be or may not be significantly different (e.g., between 0% and 30% different or anything in between these values such as between 5% and 10%) from axial compliance of a similar graft that does not have the carrier matrix attached. In FIG. 5C, as a force shown by the large arrow is applied to surgical repair graft 122" to bend surgical repair graft 122", the relatively short carrier matrix particles do not contact each other. Sections of biotextile layer 122" between attached particles 126" are able to compress and the opposing side of layer 122" is free to stretch apart and the graft is free to bend.

FIG. 6D, FIG. 6E, and FIG. 6F show side views of a surgical repair graft with a plurality of relatively tall attached carrier particles at rest and under different types of tension.

FIG. 6D shows surgical repair graft 132 at rest without added tension. FIG. 6E shows surgical repair graft 132' placed under an axial tension wherein the graft is axially stretched. FIG. 6F shows surgical repair graft 132" when the graft is placed under a bending tension and the graft is bent. In FIG. 6E, carrier matrix particles 136' are attached to layer 134 of surgical graft 132. In FIG. 6E, as a stretching tension in the direction shown by the arrow in FIG. 6E is applied to graft 134' to axially stretch layer 132', sections of layer 132' in between attached particles 136' (particle "nodes") are free to stretch in response to the stretching and the graft stretches. Axial compliance of the graft having the relatively tall carrier matrix particles attached may be or may not be significantly different (e.g., between 0% and 30% different or anything in between these values such as between 5% and 10%) from axial compliance of a similar graft that does not have the carrier matrix attached. In FIG. 6F, as a force shown by the arrow is applied to graft 132" to bend graft 132". The relatively tall particles contact each other even when the graft is bent only slightly and the bend resistance of the graft having the carrier matrix attached to it is significantly greater than the bend resistance of a similar graft that does not have carrier matrix attached. Depending on a patient's needs, a graft or a portion of a graft according to FIG. 6D, FIG. 6E, and FIG. 6F may be useful in an area of the body for which greater bend resistance is desired or unimportant. Such a graft with a relatively larger particle size may allow more active agent to be delivered.

FIG. 7A and FIG. 7B show views of another surgical repair graft having a relatively homogenous covering of carrier matrix. FIG. 7A shows surgical repair graft 152 at rest without added tension. FIG. 7B shows surgical repair graft 152' under added tension. FIG. 7A shows surgical graft 152 with covering 156 on biotextile layer 154. In FIG. 7B, as a stretching tension shown by the arrows 157a-157d is applied to graft 152' to axially stretch layer 154'. In FIG. 7B, covering 156' limits the ability of underlying biotextile layer 154' to stretch, and graft 152' stretches just to the dotted lines. In other examples, a covering and graft may stretch further. Such a covering may be very thin (and reduce a moment of inertia), such as less than 10 nm, less than 100 nm, less than 1 um, less than 100 um, less than 500 um or more than any of these values (or any values or range of values in between these values) in thickness. A covering may be a lasting (permanent or non-biodegradable) or may be biodegradable in part or in whole. A covering may be relatively uniform or may have regions of differing thickness with a first region with a first thickness and a second region with a second thickness. A carrier matrix covering may be applied to a graft, a biotextile layer or an adhesive as a plurality of separate particles to coat the graft (such as by solution or electrospray) or carrier matrix may be applied to a graft, biotextile layer, or adhesive as a sheet. In some examples, a sheet of carrier matrix may include or be combined with other components, such as an adhesive.

A covering may be a foam and may have a plurality of cells and pores. Cells going through a covering may bend and turn within the covering. In some examples, cells in a covering may be open (e.g., at least half of its cells are open via pores at the surface). In some examples, cells in a covering may be closed (having cells totally enclosed by walls). In general a closed foam covering has less than half of its cells open. Open cells in a covering may better allow bodily fluid to penetrate and may be used to control a rate of degradation. Different ratios of open cells to closed cells may provide advantages for different purposes. In some examples, having more open cells may allow a faster degradation while having fewer open cells may slow down degradation and allow agent release over a longer period of time. The presence of cells and pores in a covering may allow a covering to stretch and bend. In some examples, a covering may have up to 10 pores per square inch (PPI), from 10 to 100 pore per square inch, more than 100 and fewer than 1000 pores per square inch. Cells (over the whole graft or a region of the graft, such a square inch region) may have an average pore diameter or average cell diameter of between 10 nm and 1 mm, or anything in between, such as between 0.1 and 0.5 mm, 0.1 mm and 0.5 mm, 0.5 mm and 1 mm, etc. Such pores may also allow a fluid, such as a bodily fluid, to flow through the graft and aid in biodegrading the carrier matrix. The number and sizes of pores or cells may be chosen, for example, to control a rate of carrier matrix biodegradation and active agent release in a time sensitive manner such as releasing from 1% to 100% or of an agent (or any amount in between such as 10%, 20%, 30%, 40%, 50%, 60%, 70%, 80%, or 90%) in 1 hour to 24 hours, 1 day to 14 days, 1 week to 4 weeks or 1 month to 1 year or anything in between these times (such as between 7 days and 14 days, 21 days, etc.).

FIG. 7C and FIG. 7D show views of another surgical repair graft having a relatively homogenous covering with openings. FIG. 7C shows the repair graft at rest without added tension. FIG. 7D shows the repair graft under added tension; the openings allow the covering and graft to stretch and bend. In general, openings go through the covering, from one side of the covering to the other side. FIG. 7C shows surgical graft 162 with covering 166 on biotextile layer 164. Covering 166 can be up any thickness, but in general may be relatively thin (less than 500 nm, less than 100 nm, less than 10 nm, less than 1 nm, less than 100 um, or less than 10 um in thickness or any value or range of values in between these). In FIG. 7D, as a stretching tension shown by the arrows 167a-167d is applied to graft 162', openings 168 open, lengthen, or widen in response to the stretching tension, relieving axial tension, and covering 166' and underlying layer 164' are free to bend, expand, flex, lengthen, stretch or widen (e.g., in the X, Y, and/or Z directions) in response to the stretching force. Axial compliance (in the lengthwise (167a-167b) or widthwise (167c-167d) directions or diagonally) of graft 162' of the graft having a covering with opening may be not significantly different (e.g., between 0% and 30% different or anything in between these values such as between 5% and 10%) from axial compliance of a similar graft that does not have the carrier matrix attached. The covering with openings may readily bend when the graft is subject to a bending force and bends. Bend resistance of graft 162' having a carrier matrix covering with openings may be not significantly different (e.g., between 0% and 30% different or anything in between these values such as between 5% and 10%) from bend resistance of a similar graft that does not have the carrier matrix attached. A graft having covering with openings may additionally have any of the characteristics or properties indicated above for FIG. 7A and FIG. 7B, such as cells, pores, etc.

Openings may be substantially closed (e.g., be slits and the sides of the opening opposed or touching) when a graft is at rest and the openings only open up when the graft is subject to a force, such as an axial force or a bending force or the openings may be open or partially open even in the absence of an applied force. The openings may be any shape when opened, e.g., circular, long rectangular, diamond, etc. The openings in the covering may be randomly spaced from each other or may be regularly (geometrically) spaced from one another such as in an array or matrix. In some examples, a coating may have up to 10 openings per square inch (e.g., may have 1, 2, 3, 4, 5, 6, 7, 8, 9 openings per square inch), from 10 to 100 openings per square inch, or more than 100 openings and less than 1000 openings per square inch (or anything or range in between any of these values). Openings (over an entire graft or a region of a graft, such a square inch region) may have an average opening diameter or maximum dimension between 10 nm and 10 mm, or anything in between, such as from 0.1 mm to 0.5 mm, from 0.5 mm to 1 mm, etc. Such openings may also allow a fluid, such as a bodily fluid, to flow through the graft and aid in biodegrading the carrier matrix. The number and sizes of openings may be chosen, for example, to control a rate of carrier matrix biodegradation and active agent release in a time sensitive manner such as releasing from 1% to 100% or of an agent (or any amount in between such as 10%, 20%, 30%, 40%, 50%, 60%, 70%, 80%, or 90%) over 1 hour to 24 hours, 1 day to 14 days, 1 week to 4 weeks or 1 month to 1 year or anything or any range in between these values.

FIG. 8A, FIG. 8B, and FIG. 8C show side views of a surgical repair graft with carrier matrix attached to a biotextile layer through an intermediate adhesive. FIG. 8A shows surgical repair graft 182 at rest without added tension. FIG. 8B shows surgical repair graft 182' when the graft is subject to an axial force and the graft is axially stretched. FIG. 8C shows surgical repair graft 182" when the graft is subject to a bending force and the graft is bent.

In FIG. 8A, carrier matrix particles 186 are attached through adhesive 188 to biotextile layer 184 of surgical graft 182. In FIG. 8B, as a stretching (axial) tension in the direction shown by the large arrow in FIG. 8B is applied to graft 184', sections of adhesive 188' and underlying biotextile layer 182' in between attached particles 186' (particle "nodes") are free to stretch in response to the axial tension. Axial compliance of the graft having an adhesive attached may be or may not be not significantly different (e.g., between 0% and 30% different or anything in between these values such as between 5% and 10%) from the axial compliance of a similar graft that does not have the adhesive attached. FIG. 8A, FIG. 8B, and FIG. 8C also show carrier particles attached to the biotextile layer at an attachment end and are unattached to the biotextile layer at an unattached end. FIG. 8A, FIG. 8B, and FIG. 8C show carrier matrix particles are larger at an attachment end whereby they are attached through an adhesive to a biotextile layer and smaller at a free end whereby they are unattached to the biotextile layer. In FIG. 8A pyramidal shaped carrier matrix particles 186 are attached to adhesive 188 and through adhesive 186 to biotextile layer 184 of surgical graft 182. In FIG. 8B, as a stretching tension shown by the arrow in FIG. 8B is applied to graft 184' to axially stretch the graft, sections of adhesive 188' and biotextile layer 182' in between attached particles 186' (particle "nodes") are free to stretch in response to the axial force. Axial compliance of the graft having carrier matrix attached may be or may not be not significantly different (e.g., between 0% and 30% different or anything in between these values such as between 5% and 10%) from the axial compliance of a similar graft that does not have the carrier matrix attached. Axial compliance of the graft having both adhesive and carrier matrix attached may be or may not be not significantly different (e.g., between 0% and 30% different or anything in between these values such as between 5% and 10%) from the axial compliance of a similar graft that does not have the adhesive and carrier matrix attached.

In FIG. 8C, a bending force shown by the large curved arrow is applied to graft 182" to bend graft 182". Adhesive 188" may be sufficiently flexible such that bend resistance of graft 182" having either or both adhesive 188" and carrier matrix 186" attached may be or may not be not significantly different (e.g., between 0% and 30% different or anything in between these values such as between 5% and 10%) from the bend resistance of a similar graft that does not have either or adhesive and carrier matrix attached. Since attached particles 186" narrow from between an attached end and an unattached end (a free end not attached to the biotextile layer), attached particles 186" do not bump into each other when graft 182" bends. Sections of layer 182" between attached particles 186" are able to compress together and the opposing side of layer 182" is free to stretch apart and the graft is free to bend. In this example, adhesive 188" is sufficiently thin and/or otherwise sufficiently flexible as to allow bending and graft 182" is able to bend without undue interference from either attached particles 186" or adhesive 188". Bend resistance of the graft having both adhesive and carrier matrix attached may be or may not be not significantly different (e.g., between 0% and 30% different or anything in between these values such as between 5% and 10%) from the bend resistance of a similar graft that does not have the adhesive and carrier matrix attached.

As indicated above, a surgical repair graft may include an adhesive adhering a carrier matrix to a substrate (a biotextile layer). Carrier matrix may be any such as dendrimers, liposomes, micelles, multivesicular liposomes, nanoparticles, quantum dots, non-concentric internally aqueous chambers, each chamber surrounded by a lipid membrane, the lipid membrane containing an active agent, etc. including those described herein. In some examples, a multivesicular liposome includes non-concentric internally aqueous chambers, each chamber surrounded by a lipid membrane. A carrier matrix may be applied as a coating or sheet, may be painted onto an adhesive (or substrate) electrosprayed on, printed on, 3-D printed, emulsified with an adhesive and applied, mixed with an adhesive and applied, etc. An adhesive for adhering carrier matrix particles to a biotextile layer may be a chemical or mechanical adhesive. An adhesive may hold carrier matrix on its surface or carrier matrix may be contained or embedded in the adhesive. An adhesive may have a smooth surface or may have a rough or textured surface to further hold or entrap a carrier matrix. An adhesive may have a rough surface wherein carrier matrix fills in the roughness to generate a smoother surface with less roughness than found in the adhesive without carrier matrix attached. In some examples, an adhesive may be a gel, such as a dispersion of molecules of a liquid (e.g., the carrier matrix) within a solid. In some examples an adhesive may be a polymer configured to adhere to both carrier matrix particles and to a biotextile layer. In some examples, an adhesive may be a peptide, a polymeric hydrogel or another hydrogel configured to adhere to both carrier matrix particles and to a biotextile layer or to intermediates between such components. Thus a surgical repair graft may include a hydrogel between a carrier matrix and a biotextile layer, the hydrogel adhering the carrier matrix to the biotextile layer. The adhesive (hydrogel) may be chemically bonded to a carrier matrix and may be bonded to a lipid membrane (including to a component embedded in a lipid membrane of a carrier matrix). A chemical bond between a carrier matrix and an adhesive (e.g., a hydrogel) may be a covalent bond or may be a non-covalent chemically bond and held by, e.g., hydrogen bonds, hydrophobic bonds, ionic bonds, or van der Waals interactions. A polymer or hydrogel may be coated or otherwise placed onto a biotextile layer. A hydrogel is generally a hydrophilic three-dimensional polymer swellable by or swelled with an aqueous solution (e.g., water or saline). Such a hydrogel may be naturally occurring or may be synthetic and may contain carbohydrates, nucleic acids, lipids, proteins, etc. Such a hydrogel include a polymer, a polymer mixture, a co-polymer, a gradient polymer, an interpenetrating polymer network (IPN), a semi-interpenetrating IPN, or so forth. A hydrogel may be or may be configured to be at least 50% (w/w) aqueous (e.g., by weight of the hydrogel without water), at least 60%, at least 70%, at least 80%, or at least 90% by weight (w/w) water. A polymeric hydrogel adhesive between a carrier matrix and the biotextile layer adhering the carrier to the biotextile layer may be or may include for example, alginate, cellulose, chitosan, collagen, polyhydroxyacids, derivatized cellulose, gelatin, polyanhydrides, polycaprolactone, polyhydroxy acids, polyglycolic acid, polylactic acid, polyorthoester, etc. A surgical repair graft may include a cross-linked polymer (e.g., a cross-linked polymeric hydrogel between a carrier matrix and a biotextile layer adhering carrier matrix to a biotextile layer), the cross-link deriving from acrylamide, allyl methacrylate, dimethacrylate, dimethyl suberimidate, DMS-treated collagen, dimethyl 3, 3'-dithiobispropionimidate, ethylene glycol, glutaraldehyde, N, N methylenebisacrylamide, transglutaminase, or tripolyphosphate. In some examples, transglutaminase may be utilized to cross-link components (such as adhesive, biotextile or carrier matrix, by self cross-linking (e.g., cross-linking within any of these materials) or between two different materials (e.g., between a carrier matrix such as a multivesicular liposome and an adhesive or between a carrier matrix such as a multivesicular liposome and a biotextile layer). Such an enzyme may catalyze the formation of a covalent bond to effect cross-linking. For example, transglutaminase may be incorporated into a repair graft or otherwise be used to catalyze the formation of a covalent bond between a free amine group and an acyl/alkanoyl group between two different components such as to adhere carrier matrix to a hydrogel adhesive. Such side chains may be found on side chains of certain amino acids such as lysine, glutamate, and aspartate. Amino acids may be part of or be incorporated into any of the components of a surgical graft or medical textile. In some examples, a cross-link that also occurs naturally, such as those between amino acids mediated by transglutaminase may be more readily degraded by in a patient's body by biological processes than is a non-naturally occurring cross-link, and thus the quality and quantity (e.g., amount and locations) of such cross-links may be especially useful to control the stability or degradability of a component or a surgical repair graft to control active agent release. A transglutaminase may be obtained from natural or recombinant sources and may be microbial or non-microbial and may be from fungi, or plants or other eukaryotes. Transglutaminase that may be used to generate adhesion includes transglutaminase (e.g., EC 2.3.2.13, protein-glutamine γ-glutamyltransferase, TGase).

In some examples, an adhesive may have regions (different subregions) having different properties that facilitate attachment to different components, such as to both a carrier matrix and a biotextile. For example, an amphipathic polymer may have a first region that is more biotextile-like and able to attach and/or interpenetrate with a biotextile and may have a second region that is more carrier matrix-like and able to attach and/or interpenetrate with a carrier matrix. For example, an amphipathic polymer may have a first region that is collagen-like region able to interpenetrate and bond to collagen and may have a second region that is lipophilic and able to interpenetrate and bond to lipid membranes of a carrier matrix. In some examples, an adhesive may have one or more material gradients that allow a gradual transition from characteristics of a first region to characteristics of a second region, such as from more biotextile-like properties to more carrier matrix like properties. Materials such as those or similar to those described in U.S. Pat. Nos. 8,236, 342, 8,853,294, US201000010114, WO2017/223462, WO2017/191276 may be used.

In some examples, an adhesive, such as a polymer, polymeric hydrogel, or other hydrogel may contain a carrier matrix having an encapsulated active agent. Such an adhesive may release carrier matrix and active agent in response to adhesive degradation, diffusion of active agent through the carrier matrix and adhesive, or in response to an applied stimulus, such as a pH change, application of an electric field, application of a magnetic field, change in temperature, treatment with ultrasound and so on.

The surgical grafts described herein may have contain particles in any density, from a homogenous covering to separated particles. Particles may be separated from each other by (on an average) at least 1 nm, at least 10 nm, at least 100 nm, at least 1 µm, at least 10 µm, or at least 100 µm or any values or range of values in between these.

One or more components in a surgical repair graft may be modified or treated to change the biomechanical properties of the component(s) or graft and/or to join two or more components together. Any of the grafts or graft modifications as described in U.S. Pat. Nos. 9,775,700, 9,820,843, U.S. 2017/0000597, U.S. 2017/0020646, or U.S. 2017/0020647 may be used, alone or in combination. Any of these surgical repair grafts may further include compliance control devices that provide compliance control and/or hold two or more than two layers together. A surgical repair graft such as described herein may have one or more than one biotextile layer with a pattern of reinforced discrete compliance control sites having a density of sites that is fewer than about 10 attachments/mm$^2$. A surgical repair graft of as described herein may have one or more than one biotextile layer biotextile layer with a pattern of reinforced discrete compliance control sites having a density of sites that is between 10 attachments/mm$^2$ and 100 attachments/mm$^2$ or anything in between these values. A surgical repair graft of as described herein may have one or more than one biotextile layer biotextile layer with a pattern of reinforced discrete compliance control sites having a density of sites that is less than between 100 attachments/mm$^2$ and 500 attachments/mm$^2$ or anything in between these values. In some particular examples, stitches are those described in U.S. 2017/0020646 and may be sewn or embroidered into one or more biotextile (or adhesive) layers. Such stitches may be compliance control stitch patterns and may be configured to control the compliance of the surgical repair graft. Mechanical properties of a surgical implant may be described by stiffness, breaking strain, and maximum force. For example, material property may be described force per unit width, such as N/cm. For example, compliance strain of the biotextile layer or graft with (or without compliance control stitches) may be between 10-30% at 16 N/cm. Stitches may include a plurality of lines and/or a plurality of repeating angles oriented at one or more axes of a substrate. Stitches may form a corner-lock stitch pattern. Stitches may be non-resorbable (permanent) or may be bioresorbable. Any of these surgical repair grafts may include stitches made from a polymer such as polyethylene or polypropylene and may be a monofilament yarn or thread. Such stitches may form openings that may aid in bioresorbing an active agent from a carrier matrix. Two or more components in a graft may be joined together by an adhesive. For example, two or more biotextile layers may be joined to each other by an adhesive or a carrier matrix may be joined to a biotextile layer by an adhesive. An adhesive may be a chemical adhesive or a material adhesive. The discrete attachment sites may be chemical or material adhesives between the layer and the discrete locations, such as an adhesive or glue material that is biocompatible and adheres a first (e.g., ECM) layer to the second layer. An adhesive may be any appropriate biologically compatible adhesive. The discrete attachment sites may refer to relatively small diameter regions which may be regularly shaped or irregularly shaped and may be uniaxial or biaxial. Any of these surgical repair grafts may further include stitches sewn between two components. Any of these surgical repair grafts may further include discrete attachment sites with an attachment material (e.g., fiber, thread, yarn, etc.). For example, the discrete attachment sites may have a diameter of between about 0.001 inch and 0.20 inches (e.g., between about 0.001 inches to about 0.010 inches, between about 0.001 to about 0.060 inches, etc.). In general, the attachment between the first layer (substrate layer) and the second layer may be configured to flexibly attach the two layers, so that the attachment of the two layers does not change the compliance more than a nominal (e.g., 15% or less) amount. The density of the discrete attachment sites may be uniform or non-uniform. As mentioned above, the discrete attachment sites may be distributed in a pattern such as a grid (or overlapping grids).

Two or more than two biotextile layers in a graft (such as described herein) may be joined together. In some examples a second biotextile layer may be (flexibly) attached to a first biotextile layer in a pattern of discrete attachment sites having a density of 10 or fewer than 10 attachment sites/mm2 (e.g., 1, 2, 3, 4, 5, 6, 7, 8, or 9 attachment sites per mm$^2$). In some examples, a second biotextile layer may be (flexibly) attached to a first biotextile layer in a pattern of discrete attachment sites having a density of between 10 attachment sites/mm$^2$ and 100 attachment sites/mm$^2$. In some examples, a second biotextile layer may be (flexibly) attached to a first biotextile layer in a pattern of discrete attachment sites having a density of more than 100 attachment sites/mm$^2$. In some examples, a carrier matrix is between two biotextile layers and may be adhered to one or both of the layers.

A surgical repair graft that includes a carrier matrix or an adhesive (or both considered together) may alter a compliance (e.g., an axial tensile compliance; force per unit stretch) of a surgical repair graft having similarly stacked layers not having the carrier matrix by less than 50%, less than 40%, less than 30%, less than 20%, less than 25% less than 10%, less than 5% or anything in between. In some examples, the presence of a carrier matrix in a surgical repair graft decreases the compliance of the graft compared with a repair graft having similarly stacked layers not having the carrier matrix. A compliance of surgical repair graft may not change or may increase over time when the carrier matrix is exposed to a bodily fluid or an aqueous fluid. A compliance may increase by up to 5%, up to 10%, up to 15%, up to 20%, up to 25%, up to 30%, up to 35%, up to 40%, up to 50%, or less than 5%, less than 10%, less than 15%, less than 20%, less than 25%, less than 30%, less than 35%, less than 40%, less than 50% or anything in between such as up to 25% and less than 50% compared with a repair graft having similarly stacked layers not having the carrier matrix. The compliance may be measured over any time period, such as one day, from one day to fourteen days, from one week to four weeks, from four weeks to twenty six weeks, from twenty six weeks to fifty two weeks or anything in between these amounts, such as after 8 weeks. In some examples, the compliance may be measured after one or more than one more year. In any of these cases, the remainder of the surgical repair graft may remain intact, thus the (stacked) biotextile layers of the surgical repair graft may remain intact and stacked. A compliance strain of a surgical repair graft as described here may between 10-30% at 16 N/cm (e.g., prior to exposure to a bodily fluid for any of the times and conditions described herein, after exposure to a bodily fluid for any of the times and conditions described herein, or both before and after exposure to a bodily fluid for any of the times and conditions described herein).

A surgical repair graft that includes a carrier matrix or an adhesive (or both considered together) including any type of stitch may alter a uniaxial tension of a surgical repair graft having similarly stacked layers not having the carrier matrix by less than 50%, less than 40%, less than 30%, less than 20%, less than 25% less than 10%, less than 5%, less than 1% or anything in between. In some examples, the presence of a carrier matrix in a surgical repair graft decreases the uniaxial tension of the graft compared with a repair graft having similarly stacked layers not having the carrier matrix. A uniaxial tension of a surgical repair graft may increase over time when the carrier matrix is exposed to a bodily fluid or an aqueous fluid. A uniaxial tension may increase by up to 5%, up to 10%, up to 15%, up to 20%, up to 25%, up to 30%, up to 35%, up to 40%, up to 50%, or less than 5%, less than 10%, less than 15%, less than 20%, less than 25%, less than 30%, less than 35%, less than 40%, less than 50% or anything in between such as up to 25% and less than 50% compared with a repair graft having similarly stacked layers not having the carrier matrix. The uniaxial tension may be measured over any time period, such as one day, from one day to fourteen days, from one week to four weeks, from four weeks to twenty six weeks, from twenty six weeks to fifty two weeks or anything in between these amounts, such as after 8 weeks. In some examples, the uniaxial tension may be measured after one or more than one more year. In any of these cases, the remainder of the surgical repair graft may remain intact, thus the (stacked) biotextile layers of the surgical repair graft may remain intact and stacked.

A surgical repair graft that includes a carrier matrix or an adhesive (or both considered together) may alter a bending stiffness of a surgical repair graft having similarly stacked layers not having the carrier matrix by less than 50%, less than 40%, less than 30%, less than 20%, less than 25% less than 10%, less than 5%, less than 1% or anything in between. In some examples, the presence of a carrier matrix in a surgical repair graft decreases a bending stiffness of the graft compared with a repair graft having similarly stacked layers not having the carrier matrix. A bending stiffness of a surgical repair graft may increase over time when the carrier matrix is exposed to a bodily fluid or an aqueous fluid. A uniaxial tension may increase by up to 5%, up to 10%, up to 15%, up to 20%, up to 25%, up to 30%, up to 35%, up to 40%, up to 50%, or less than 5%, less than 10%, less than 15%, less than 20%, less than 25%, less than 30%, less than 35%, less than 40%, less than 50% or anything in between such as up to 25% and less than 50% compared with a repair graft having similarly stacked layers not having the carrier matrix. A bending stiffness may be measured over any time period, such as one day, from one day to fourteen days, from one week to four weeks, from four weeks to twenty six weeks, from twenty six weeks to fifty two weeks or anything in between these amounts, such as after 8 weeks. In some examples, a bending stiffness may be measured after one or more than one more year. In any of these cases, the remainder of the surgical repair graft may remain intact, thus the (stacked) biotextile layers of the surgical repair graft may remain intact and stacked.

A surgical repair graft that includes a carrier matrix or an adhesive (or both considered together) may alter a burst strength of a surgical repair graft having similarly stacked layers not having the carrier matrix by less than 50%, less than 40%, less than 30%, less than 20%, less than 25% less than 10%, less than 5%, less than 1% or anything in between. In some examples, the presence of a carrier matrix in a surgical repair graft decreases or increases a burst strength of the graft compared with a repair graft having similarly stacked layers not having the carrier matrix. A burst strength of a surgical repair graft may decrease or increase over time when the carrier matrix is exposed to a bodily fluid or an aqueous fluid. A burst strength may change by up to 5%, up to 10%, up to 15%, up to 20%, up to 25%, up to 30%, up to 35%, up to 40%, up to 50%, or less than 5%, less than 10%, less than 15%, less than 20%, less than 25%, less than 30%, less than 35%, less than 40%, less than 50% or anything in between such as up to 25% and less than 50% compared with a repair graft having similarly stacked layers not having the carrier matrix. A burst strength may be measured over any time period, such as one day, from one day to fourteen days, from one week to four weeks, from four weeks to twenty six weeks, from twenty six weeks to fifty two weeks or anything in between these amounts, such as after 8 weeks. In some examples, a burst strength may be measured after one or more than one more year. In any of these cases, the remainder of the surgical repair graft may remain intact, thus the (stacked) biotextile layers of the surgical repair graft may remain intact and stacked.

A surgical repair graft that includes a carrier matrix or an adhesive (or both considered together) may alter a roughness of a surgical repair graft having similarly stacked layers not having the carrier matrix by less than 50%, less than 40%, less than 30%, less than 20%, less than 25% less than 10%, less than 5%, less than 1% or anything in between. A roughness of a surgical repair graft may slightly decrease or increase over time when the carrier matrix is exposed to a bodily fluid or an aqueous fluid. Surface roughness may be made by any means, such as categorizing them by height, depth, and/or interval. Linear roughness or areal roughness (over a rectangular range) may be measured using contact or non-contact (e.g., optical) methods.

Figure 9B:
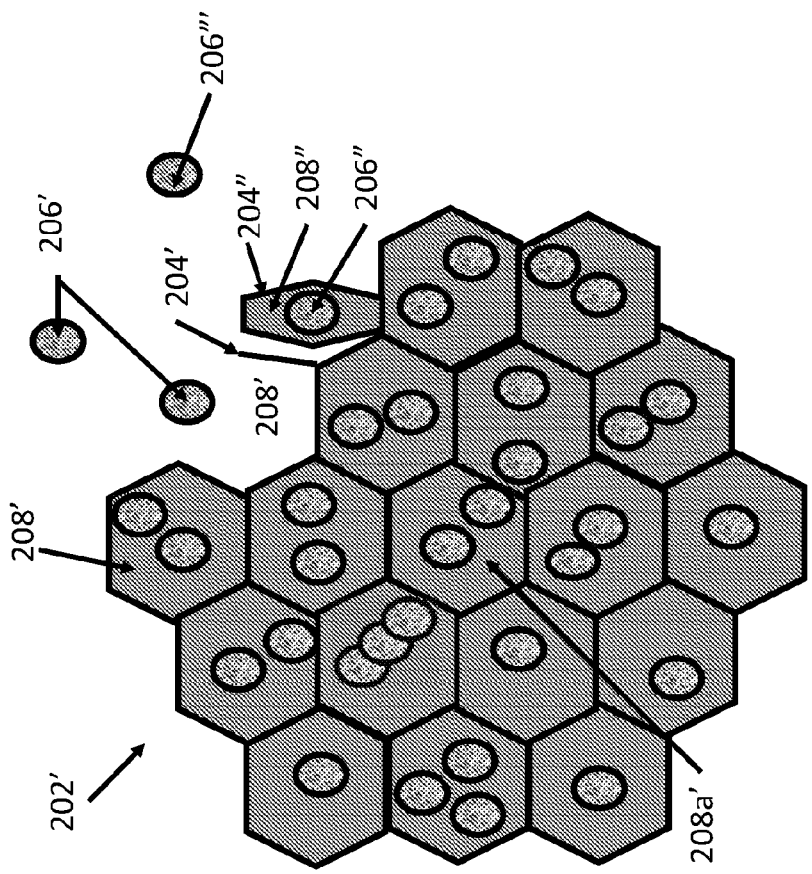
FIG. 9B shows a partially degraded version of the carrier matrix particle shown in FIG. 9A.
Figure 9A:
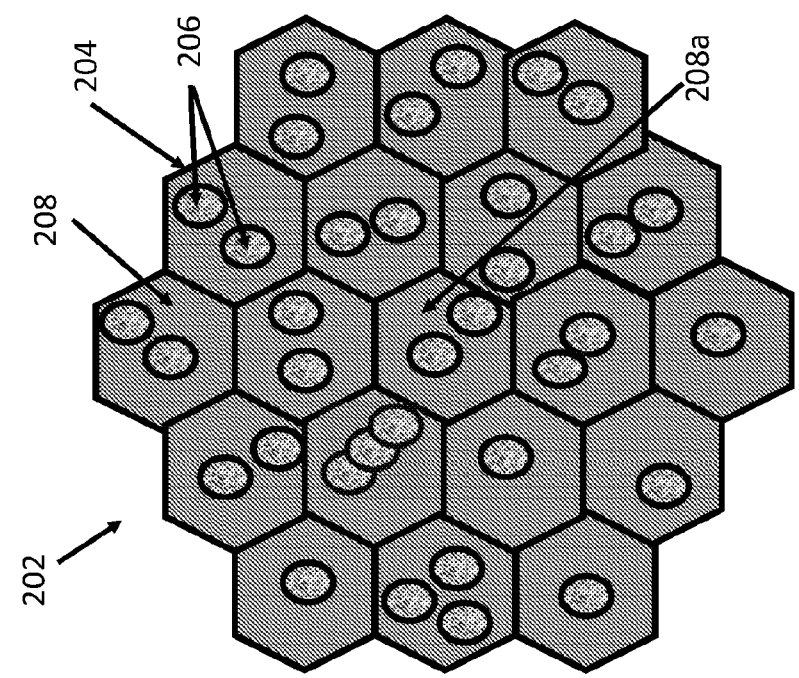
FIG. 9A shows a carrier matrix particle having a plurality of non-concentric internally aqueous chambers each surrounded by a lipid membrane and containing an agent (e.g., a drug).

FIG. 9A shows carrier matrix particle 202 having a plurality of non-concentric internally aqueous chambers 208 each surrounded by lipid membrane 204 and containing first agent 206. FIG. 9B shows a partially degraded version of carrier matrix particle 202' of FIG. 9A. Lipid membrane 204' is partially degraded and the contents of chamber 208' including agent 206' is being released from the particle. In another region of the particle, lipid membrane 204" has reorganized around internally aqueous chamber 208" and agent 206" and part of the contents of the chamber has been released as shown by the presence of agent 206''' outside the carrier matrix particle. FIG. 9B also shows an external part of the particle (e.g., chamber 208' and chamber 208") that degrades and/or reorganizes prior to an internal region 208a of the particle degrading or reorganizing. (Internal region 208a is the same as internal region 208a'). In some examples, a carrier matrix particle does not readily degrade or reorganize and the carrier matrix particle may serve to hold an agent in its chambers. Such a particle may have a structure such as that shown in FIG. 9A, FIG. 10A, FIG. 11A, or FIG. 12A or variations thereof.

FIG. 10A shows a carrier matrix particle 212 having a plurality of non-concentric internally aqueous chambers 208 each surrounded by lipid membrane 204 and containing first agent 206 and second agent 214 in different chambers. FIG. 10B shows a partially degraded version of carrier matrix particle 212' of FIG. 10A. Lipid membrane 204' is partially degraded and the contents of chamber 208' including first agent 206' and second agent 214' is being released.

FIG. 11A shows carrier matrix particle 222 having a plurality of non-concentric internally aqueous chambers 208 each surrounded by lipid membrane 204 and containing first active agent 206 and second active agent 214 in the same chamber 208. FIG. 11B shows a partially degraded version of carrier matrix particle 222' of FIG. 11A. Lipid membrane 204' is partially degraded and the contents of chambers 208' including first agent 206' and second agent 214' is being released.

Figures 12A, 12B:
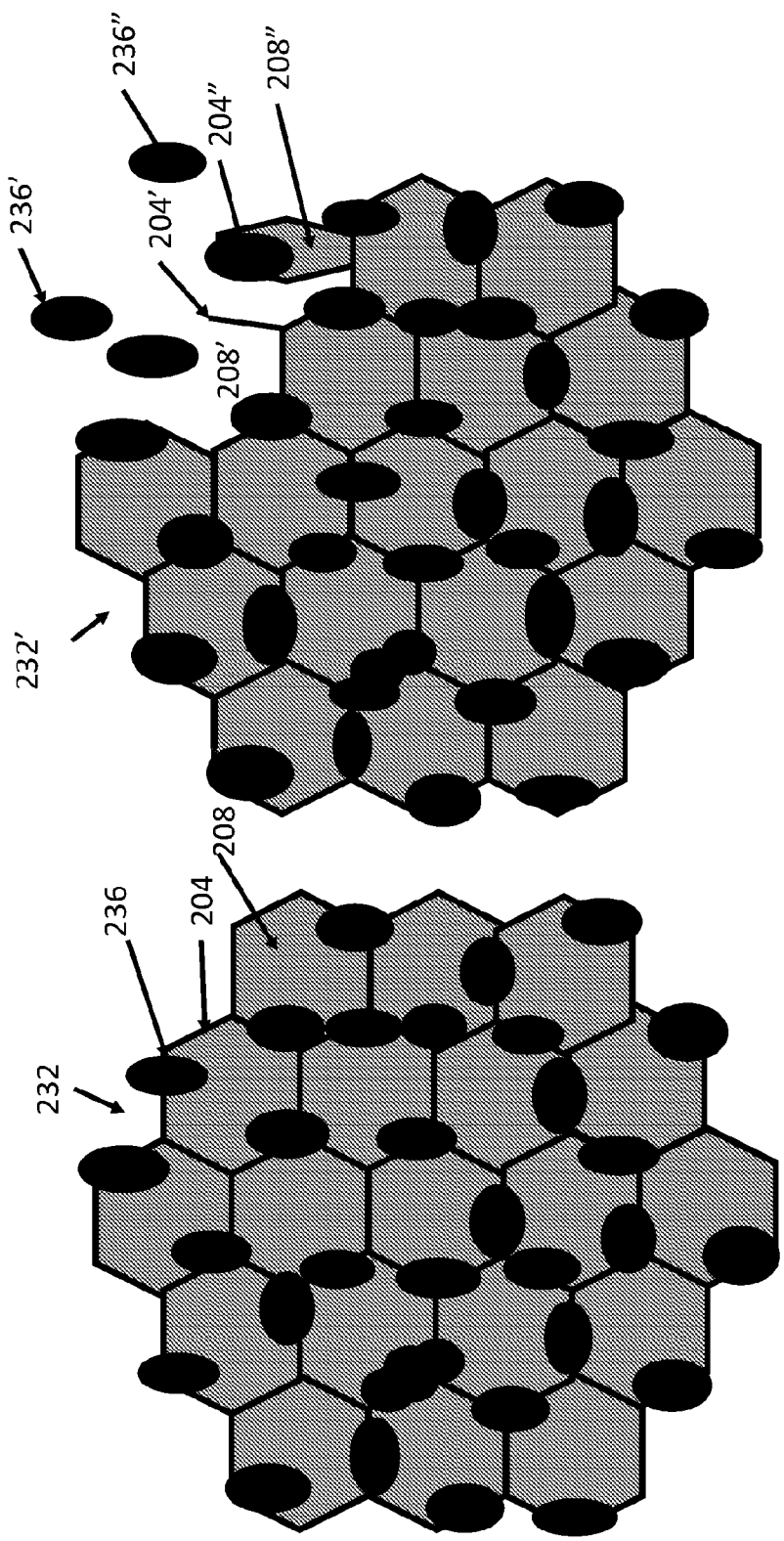
FIG. 12A shows a carrier matrix particle having a plurality of non-concentric internally aqueous chambers each surrounded by a lipid membrane and containing an agent in the lipid membrane.
FIG. 12B shows a partially degraded version of the carrier matrix particle shown in FIG. 12A.

FIG. 12A shows carrier matrix particle 232 having a plurality of non-concentric internally aqueous chambers 208 each surrounded by lipid membrane 204 and containing first agent 236 which is lipophilic and substantially entrapped or embedded in lipid membrane 204. FIG. 12B shows a partially degraded version of carrier matrix particle 232' of FIG. 12A. Lipid membrane 204' is partially degraded and the contents of chamber 208' including first agent 236' which is lipophilic is being released. In some examples, a carrier matrix particle reorganizes as shown by reorganized membrane 204" containing reorganized chamber 208". First agent 236" has moved along with reorganized membrane 204" as it reorganized and is still entrapped or embedded within. First agent 236''' has been released due to the reorganization of reorganized membrane 204".

A surgical repair graft may have a biotextile layer; and a carrier matrix attached to the biotextile layer and comprising a plurality of particles each having a plurality of non-concentric internally aqueous chambers surrounded by a lipid membrane, one or more of the membrane and the aqueous chambers containing an agent. Thus an internally aqueous chamber may carry an (active) agent and/or a lipid membrane may carry an (active) active agent. Alternatively, a carrier matrix may not have such chambers and membrane and may carry an agent. A carrier matrix particle (a liposome) may act as a depot from which an entrapped agent can be slowly released. This may serve to maintain therapeutic levels of the agent in the blood, at the release site, or in another location in a body. In some examples, a therapeutic level of an active agent is from 5% to 100% or anything in between of a $C_{max}$ of an immediate release dosage form of an active agent. An internally aqueous chamber may include a buffer, a hydrogel, etc. In some examples, a plurality of particles may be DepoFoam particles. An agent carried in an aqueous chamber may be carried as a colloid in the aqueous material, may be dissolved in the aqueous material, or so on. An agent carried in an aqueous chamber may be charged, hydrophilic, polar etc. such that it is readily carried in an aqueous material. An agent carried in a lipid membrane in general is lipophilic or is coated or otherwise treated to be lipophilic. Such an agent may be hydrophobic or neutral (uncharged). An agent may be an active agent such as an active ingredient or an active pharmaceutical ingredient (API) and may be an agent useful for diagnosing, imaging, managing, preventing or treating such as for diagnosing, imaging, managing, preventing and/or treating anxiety, asthma, attention deficit disorder, bipolar disorder, cancer, diabetes, dementia, depression, a disease, a disorder, an eating disorder, inflammation, infection, mental illness, a neurological disorder, pain, panic, sleep disorder, etc. An agent may be an active agent such as an active pharmaceutical ingredient (API) approved by the United States Food and Drug Administration/Center for Drug Evaluation and Research and may be a brand name, generic or an over-the-counter pharmaceutical agent. An agent may be an antidepressant, an antineoplastic agent, an anxiolytic, antisense oligonucleotide, an antibiotic, an antifungal agent, an antipsychotic, an antithrombolytic, a cell, a drug, a DNA, a fungicide, a hormone, an RNA, an immunoglobulin E blocker (IgG), a non-steroidal anti-inflammatory agent, an opioid, a pain reliever (pain medication), a peptide, a protein, an antirheumatic agent, a sedative, a sense oligonucleotide, a small drug, a steroid. An agent may be radiopaque. In a particular example, an agent is bupivacaine or salts of bupivacaine or variations thereof. An agent may be 5-azacytidine, amikacin, amitriptyline, ampicillin, aripiprazole, betamethasone, chlordiazepoide, chlorpromazine, corticosteroid, cyanocobalamine, cytarabine, daunorubicin, decitabine, delatestryl, delestrogen, desferrioxamine, desferrioxamine mesylate, desmopressin, desmopressin acetate, desoxycorticosterone pivalate, enoxaparin, exenatide, fentanyl, fluphenazine, gentamicin, haloperidol, heparin, hydromorphone, hydromorphone HCL, imitrex, insulin, leuprolide, loflupane, lorazepam, medroxyprogesterone, methotrexate, methylprednisolone, methylprednisolone acetate, morphine, morphine sulfate, naloxone, naltrexone, nandrol decanoate, octreotide acetate, omalizumab, olanzapine, paclitaxel, paliperidone, penicillin, penicillin G benzathine, penicillin G procaine, progesterone, risperidone, terbutaline, testosterone, testosterone cypionate, testosterone enanthate, triamcinolone acetonide, triptorelin, and salts and variations thereof. A carrier matrix may also contain one or more than one inactive ingredients that do not have a pharmacological or therapeutic effect on the body, such as a binding agent, a coating, a coloring agent, a disintegrant, an excipient, enzyme, a filler, a preservative, a stabilizer, etc.

In some examples, a carrier matrix particle generally has a plurality of aqueous chambers each surrounded by a lipid membrane. In some examples, a carrier matrix particle has a plurality of non-concentric internally aqueous chambers each surrounded by lipid membrane and containing an agent in at least one of the membrane and the chambers. In general a lipid membrane of a carrier matrix particle is biocompatible and is configured to biodegrade although in some cases it may not biodegrade and instead may be stable over time. In some examples, an enzyme may be present in a surgical graft or carrier matrix and may function to biodegrade the surgical graft or carrier matrix or may change (breakdown) an agent from an inactive form into an active agent. For example, an enzyme may break down a prodrug into a drug that has a therapeutic effect on the body. A biodegradable material, such as a lipid membrane of a carrier matrix particle, is a material may be broken down and cleared by the body's normal metabolic pathways. A lipid membrane of a carrier matrix particle may naturally occurring lipids or synthetic lipids including synthetic versions of a lipid(s) naturally found in the body. Naturally occurring types of lipids may be those generally found in the body (e.g., a human or mammalian body). A lipid membrane may be a lipid monolayer, a lipid bilayer, a lipid trilayer, etc. A lipid membrane of a carrier matrix particle may be neutral, may be polar, or may be charged. In a particular example a lipid membrane is a phospholipid bilayer. In some examples, a lipid membrane includes an amphipathic lipid or salt thereof, one or more neutral lipids, and optionally cholesterol and/or plant sterols. In some examples a carrier matrix particle includes a multivesicular liposome have at least one amphipathic lipid, at least one neutral lipid, and a therapeutic agent. In some examples, a lipid membrane of a carrier matrix particle includes phospholipids, cholesterol, and triglycerides. In some examples, a phospholipid is dioleoylphosphatidylcholine (DOPC). In some versions, the triglyceride is a synthetic version of a lipid found in the body, such as tricaprylin. In some examples, carrier matrix particle is from 1% (w/w) to 10% (w/w) lipid or anything in between such (1% (w/w), 2% (w/w), 3% (w/w), 4% (w/w), 5% (w/w) 6% (w/w), 7% (w/w), 8% (w/w), 9% (w/w), and 10% (w/w) or from between any of these, such as from 3% (w/w) to 6% (w/w) or from 8% (w/w) to 9% (w/w). In some examples, carrier matrix particle is from 10% (w/w) to 20% (w/w) lipid. Part (e.g., an outer part, an inner facing part) of a carrier matrix particle may be neutral, polar, or charged and another part may have different properties (e.g., an inner facing surface may be neutral while an outer facing surface is charged, etc.). In some examples, an outer facing surface of a lipid membrane is complementary to an adhesive material such that an adhesive membrane adheres to or binds (e.g., chemically binds) to an outer facing surface of a lipid membrane. For example, an outer facing surface of a lipid membrane may be negatively charged and an adhesive positively charged such that the adhesive binds to the outer facing surface of the membrane. An outer facing surface may be modified with proteins or amino groups which may be attached such as through amino groups or sulfhydryl groups.

A carrier matrix particle(s) can be from 80% (w/w) aqueous material to 99% aqueous material or anything or any range in between. In some examples, a carrier matrix particle(s) can be from 90% (w/w) aqueous material to 95% aqueous material of any range in between. Thus a carrier matrix particle can be 80% (w/w), 81% (w/w), 82% (w/w), 83% (w/w), 84% (w/w), 85% (w/w), 86% (w/w), 87% (w/w), 88% (w/w), 89% (w/w), 90% (w/w), 91% (w/w), 92% (w/w), 93% (w/w), 94% (w/w), 95% (w/w), 96% (w/w), 97% (w/w), 98% (w/w), and 99% (w/w) aqueous material or anything in between such as from 92% (w/w) to 97% (w/w), etc. A carrier matrix particle may have a capture volume (an internal volume) of 10% to 90% or anything in between, such as 20% to 35%. A carrier matrix may have any configuration or any materials that carries an agent, such as a polymer such as cellulose esters, ethylcellulose polymer, gelatin, polycaprolactone, poly diaxonone, poly hydroxyl butyrate, poly lactic acid, poly lactide-co-glycolide (PLGA), polyester, poly glycolic acid, polyester amide, polyester urea, polyester urethane, polyethylene oxide, a water soluble resin, and so on. Such materials may be in a liquid dispersion and/or be biodegradable. A carrier matrix may contain one or more than one type of materials. The more than one type of materials may be configured to degrade or otherwise release an active agent over different times. Thus, a carrier matrix may have a first material that degrades more quickly and releases a first active agent quickly and a second material that degrades more slowly and releases a second active agent over a longer period of time. A first active agent and second active agent may be the same or may be different, including any as described herein. In some examples, a surgical graft or carrier matrix does not contain cyclodextrin.

A carrier matrix particle is generally a microscopic particle and as indicated elsewhere herein, a carrier matrix particle can be any shape. A carrier matrix particle may be from between 1 um to 500 um or longer in a longest dimension (or diameter), from 5 um, 10 um, 20 um, 30 um, 40 um, 50 um, 60 um, 70 um, 80 um, 90 um, 100 um, 200 um, 300 um, 400 um, or 500 um in a longest dimension (or diameter) or any value or range of values in between these values. In some examples, a particle is between 1 um and 60 um, between 5 um and 55 um, between 15 um and 50 um and so on. A carrier matrix particle may contain from 1 to 500 or more than 500 internal chambers, such as at least 2, at least 5, at least 10, at least 25, at least 50, at least 100, at least 200, at least 300, at least 400, at least 500, at least 1000 internal chambers or may have fewer than 1000, fewer than 500, fewer than 400, fewer than 300, fewer than 200, fewer than 100, fewer than 50, fewer than 25, fewer than 10, fewer than 5 or anything in between such as at least 50 and fewer than 300, at least 100 and fewer than 500 and so on.

Manipulation of the amounts, types and compositions of adhesives, lipids, aqueous material, and agent material may be used to control the rate and time of degradation and/or lipid membrane reorganization. Controlling the particle size may be used to control the rate and time of degradation and/or the rate and time of lipid membrane reorganization. The amounts and types of materials and other characteristics of the carrier matrix and surgical graft may be chosen, for example, to control a rate of carrier matrix biodegradation and active agent release in a time sensitive manner such as releasing from 1% to 100% or of an agent (or any amount in between such as 10%, 20%, 30%, 40%, 50%, 60%, 70%, 80%, or 90%) in 1 hour to 24 hours, 1 day to 14 days, 1 week to 4 weeks or 1 month to 1 year or anything in between these times (such as 6 days, 21 days, etc.) upon continuous exposure to a bodily fluid. In some particular examples, a carrier matrix is at least 50% degraded after 14 days upon continuous exposure to a bodily fluid or bodily fluid substitute (e.g., a synthetic version of a bodily fluid), at least 95% degraded within one day of continuous exposure to a bodily fluid, at least 95% degraded after 30 days of continuous exposure to a bodily fluid, between 25% and 75% degraded at 7 days of continuous exposure to a bodily fluid, between 25% and 75% degraded at 14 days of continuous exposure to a bodily fluid. A bodily fluid may be, for example, ascites, blood, breast milk, gastric fluid, intestinal fluid, interstitial fluid, lymph fluid, menstrual fluid, peritoneal fluid, perspiration, urine, wound exudate and so forth.

Described herein is a method for controlled release an active agent from a surgical repair graft, including exposing a surgical repair graft having one or more than one stacked biotextile layers and a bioabsorbable carrier matrix attached to the one or at least one of the biotextile layers, the carrier matrix comprising a plurality of particles each having a plurality of non-concentric internally aqueous chambers surrounded by lipid membranes, at least one of the membrane and the aqueous chambers containing an active agent; and degrading over time the lipid membrane by the aqueous fluid to thereby release the active agent from the carrier matrix.

Also described herein is a method for diagnosing, treating or otherwise relieving the symptoms of an affliction, disease, or disorder (including any of those described herein) comprising administering a formulation to a subject in need thereof by implanting a surgical repair graft having the formulation attached, wherein the formulation comprises multivesicular liposomes, the multivesicular liposomes comprising an amount of an active pharmaceutical ingredient (API), one or more amphipathic lipids or salts thereof, one or more neutral lipids, and optionally cholesterol or plant sterols, wherein the formulation is substantially cyclodextrin free, wherein administration of a single dose of said formulation to the subject in need thereof results in a plasma C max of the active pharmaceutical ingredient of from 5% to 50% of the plasma C max an of immediate release dosage forms of the active pharmaceutical ingredient, and wherein a duration of the active pharmaceutical ingredient in the subject is from about 1 to about 30 days.

Also described herein is a method of treating postoperative or post-trauma pain in a subject in need thereof comprising administering a multivesicular liposome comprising a therapeutically effective amount of an analgesic attached to a surgical repair graft, wherein the multivesicular liposome comprises the analgesic; a lipid component comprising at least one amphipathic lipid and at least one neutral lipid lacking a hydrophilic head group; and, optionally, a cholesterol and/or a plant sterol. In some particular examples, the analgesic comprises bupivacaine or a salt or derivative thereof such as bupivacaine phosphate.

In some such methods, wherein a first set of chambers is on the exterior of the particle and a second set of chambers is on the interior of the particle, lipid walls on the first set of chambers are degraded first and lipid walls on the second set of chambers are degraded later. In some such methods, wherein the one or more biotextile layer comprises pores, the method further includes flowing active agent through the pores to thereby release it to a body region adjacent one biotextile layer of the one or more biotextile layers. A body may be that of an animal or plant and a body region may be part of a body system, a body organ or part of a body organ, such as a breast, an intestine, a muscle, a stomach etc., In some such methods, wherein a hydrogel is adhered to at least one of the layers, the method further includes flowing active agent through the hydrogel to thereby release it to a body region adjacent the surgical repair graft. In some such methods, the aqueous fluid includes a bodily fluid, such as ascites, blood, breast milk, gastric fluid, intestinal fluid, interstitial fluid, lymph fluid, menstrual fluid, peritoneal fluid, perspiration, urine, wound exudate, etc. In some such methods, a compliance strain of the surgical repair graft is between 10-30% at 16 N/cm prior to the degrading step. In some such methods, a compliance strain of the surgical repair graft is between 10-30% at 16 N/cm after the degrading step. In some such methods, a compliance strain of the surgical repair graft is between 10-30% at 16 N/cm after the degrading step. In some such methods, a compliance strain of the surgical repair graft is between 10-30% at 16 N/cm both before and after the degrading step. Such compliance after the degrading step may be measured after 1 hour to 24 hours, 1 day to 14 days, 1 week to 4 weeks or 1 month to 1 year or anything in between these times (such as 6 days, 21 days, etc.) of continuous exposure to a bodily fluid.

In some methods for controlled release an active agent from a surgical repair graft, carrier matrix is at least 50% (or at least 95% or between 25% and 75%) degraded one day after beginning the exposing step. In some methods for controlled release an active agent from a surgical repair graft, carrier matrix at least 50% (or at least 95% or between 25% and 75%) degraded 14 days after beginning the exposing step. In some methods for controlled release an active agent from a surgical repair graft, carrier matrix at least 50% (or at least 95% or between 25% and 75%) degraded 90 days after beginning the exposing step. In some methods for time releasing an active agent from a surgical repair graft, carrier matrix particles are at least 50% (or at least 95% or between 25% and 75%) degraded 1 hour to 24 hours, 1 day to 14 days, 1 week to 4 weeks or 1 month to 1 year or anything in between these times (such as 6 days, 21 days, etc.) after beginning the exposing step.

In some methods for controlled release an active agent from a surgical repair graft, carrier matrix particles are between 1% (w/w) and 10% (w/w) lipid prior to the degrading step. In some methods for controlled release an active agent from a surgical repair graft, carrier matrix particles are between 1% (w/w) and 10% (w/w) lipid one day after beginning the exposing step. In some methods for controlled release an active agent from a surgical repair graft, carrier matrix particles are between 1% (w/w) and 10% (w/w) lipid 14 days after beginning the exposing step. In some methods for controlled release of an active agent from a surgical repair graft, carrier matrix particles are between 1% (w/w) and 10% (w/w) lipid 90 days after beginning the exposing step. In some methods for time releasing an active agent from a surgical repair graft, carrier matrix particles are between 1% (w/w) and 10% (w/w) lipid 1 hour to 24 hours, 1 day to 14 days, 1 week to 4 weeks or 1 month to 1 year or anything in between these times (such as 6 days, 21 days, etc.) after beginning the exposing step.

In some methods for controlled release of an active agent from a surgical repair graft, carrier matrix particles are between 80% (w/w) and 99% (w/w) aqueous prior to the degrading step. In some methods for controlled release of an active agent from a surgical repair graft, carrier matrix particles are between 80% (w/w) and 99% (w/w) aqueous one day after beginning the exposing step. In some methods for controlled release of an active agent from a surgical repair graft, carrier matrix particles are between 80% (w/w) and 99% (w/w) aqueous 14 days after beginning the exposing step. In some methods for controlled release of an active agent from a surgical repair graft, carrier matrix particles are between 80% (w/w) and 99% (w/w) aqueous 90 days after beginning the exposing step. In some methods for time releasing an active agent from a surgical repair graft, carrier matrix particles are between 80% (w/w) and 99% (w/w) aqueous 1 hour to 24 hours, 1 day to 14 days, 1 week to 4 weeks or 1 month to 1 year or anything in between these times (such as 6 days, 21 days, etc.) after beginning the exposing step.

In some methods for controlled release of an active agent from a surgical repair graft, carrier matrix particles have at least 50 (or at least 10 or at least 100) internally aqueous chambers prior to the degrading step. In some methods for controlled release of an active agent from a surgical repair graft, carrier matrix particles have at least 50 (or at least 10 or at least 100) internally aqueous chambers one day after beginning the exposing step. In some methods for controlled release of an active agent from a surgical repair graft, carrier matrix particles have at least 50 (or at least 10 or at least 100) internally aqueous chambers 14 days after beginning the exposing step. In some methods for controlled release of an active agent from a surgical repair graft, carrier matrix particles have at least 50 (or at least 10 or at least 100) internally aqueous chambers 90 days after beginning the exposing step. In some methods for time releasing an active agent from a surgical repair graft, carrier matrix particles have at least 50 (or at least 10 or at least 100) internally aqueous chambers 1 hour to 24 hours, 1 day to 14 days, 1 week to 4 weeks or 1 month to 1 year or anything in between these times (such as 6 days, 21 days, etc.) after beginning the exposing step. In some methods for time releasing an active agent from a surgical repair graft, carrier matrix particles have at least 50 (or at least 10 or at least 100) internally aqueous chambers both before the exposing step and 1 hour to 24 hours, 1 day to 14 days, 1 week to 4 weeks or 1 month to 1 year or anything in between these times (such as 6 days, 21 days, etc.) after beginning the exposing step.

In some methods for controlled release of an active agent from a surgical repair graft, the active agent comprises any active agent as described herein. In some methods for controlled release of an active agent from a surgical repair graft, the active agent includes an active pharmaceutical ingredient. In some methods for controlled release of an active agent from a surgical repair graft, the active agent includes an antifungal agent, antineoplastic agent, or an antibiotic. In some methods for controlled release of an active agent from a surgical repair graft, the active agent includes a pain reliever, e.g., an analgesia. In some methods for controlled release of an active agent from a surgical repair graft, the active agent includes bupivacaine.

In some examples, a surgical repair graft or carrier matrix may be configured to release active agent such that a therapeutic level of active agent is released into the bloodstream. In such cases, the plasma concentration of the active agent may spike at a particular concentration or may be sustained at a therapeutic concentration for one hour, from one hour to 24 hours (or anything in between, such as 8 hours or 12 hours), 1 day to 14 days, 1 week to 4 weeks or 1 month to 1 year or anything in between these times (such as 6 days, 21 days, etc.) after beginning the exposing step. For example, a drug may be bupivacaine (e.g., Exparel) and the plasma level of bupivacaine may be at least 50 ng/mL, at least 100 ng/mL, at least 500 ng/mL, at least 1000 ng/mL, at least 2000 ng/mL, at least 3000 ng/mL, at least 4000 ng/mL, at least 5000 ng/mL or anything in between, such as at least 2,500 ng/mL or between 2000 ng/mL and 4000 ng/mL. The concentration may be an FDA approved dosage. In some examples, a surgical repair graft or carrier matrix may be configured to release a therapeutic amount of an active agent, such as releasing 50 mg bupivacaine, 100 mg bupivacaine, 150 mg bupivacaine, 200 mg bupivacaine, 300 mg bupivacaine, 400 mg bupivacaine, 500 mg bupivacaine, or 1000 mg bupivacaine in a certain time period, such as in 24 hours, In some methods for controlled release of an active agent from a surgical repair graft, the method further includes an adhesive, such as a chemical or physical adhesive (and including those described herein) adhering the carrier matrix to the biotextile layer. In some methods for controlled release of an active agent from a surgical repair graft, the method further includes a polymer (e.g., a hydrogel) adhering the carrier matrix to the biotextile layer. In some methods, the hydrogel is chemically bonded (e.g., either covalently bonded or non-covalently bonded) to the biotextile layer. In some methods for controlled release of an active agent from a surgical repair graft, the method further includes a polymer (e.g., alginate, cellulose, chitosan, collagen, polyhydroxyacids, derivatized cellulose, gelatin, polyanhydrides, polycaprolactone, polyhydroxy acids, polyglycolic acid, polylactic acid, or polyorthoester) adhering the carrier matrix to the biotextile layer. In some methods for controlled release of an active agent from a surgical repair graft, the method further includes a cross-linked polymeric hydrogel between the carrier and the biotextile layer adhering the carrier to the biotextile layer, the cross-link derived from acrylamide, allyl methacrylate, dimethacrylate, dimethyl suberimidate, DMS-treated collagen, dimethyl 3, 3'-dithiobispropionimidate, ethylene glycol, glutaraldehyde, N, N methylene-bisacrylamide, transglutaminase, or tripolyphosphate.

In some methods for controlled release of an active agent from a surgical repair graft, the method further includes a second of the biotextile layers which is flexibly attached to a first of the biotextile layers with a pattern of discrete attachment sites. In some methods, a density of discrete attachment sites that is less than about 10 attachments/mm$^2$ and the number of attachment sites is substantially unchanged 30 days after the beginning of the degrading step. In some methods, a compliance of the stacked layers increases up to 10% 14 days after the beginning of the degrading step. In some methods, a compliance of the stacked layers changes by less than 5% 14 days after the beginning of the degrading step. In some methods, a uniaxial tension of the stacked layers changes by less than 10% 14 days after the beginning of the degrading step. In some methods, uniaxial tension of the stacked layers changes by less than 5% 14 days after the beginning of the degrading step. In some methods, a bending stiffness of the stacked layers changes to 10% 14 days after the beginning of the degrading step. In some methods, a bending stiffness of the stacked layers changes by less than 5% 14 days after the beginning of the degrading step. In some methods, a burst strength of the stacked layers increases up to 10% 14 days after the beginning of the degrading step. In some methods, a burst strength of the stacked layers changes by less than 5% 14 days after the beginning of the degrading step. In some methods, a roughness of the stacked layers changes by less than 20% 14 days after the beginning of the degrading step. In some methods, a roughness of the stacked layers increases up to 10% 14 days after the beginning of the degrading step. In some methods, a roughness of the stacked layers changes by less than 5% 14 days after the beginning of the degrading step. In some methods, a stiffness of the surgical mesh changes by less than 10% when at least 50% of the carrier matrix is degraded by exposure to aqueous fluid for at least 14 days.

Also described herein are methods of manufacturing a surgical repair graft. A method of manufacturing a surgical repair graft includes hydrating a biotextile layer having a first compliance; adhering to the biotextile layer a carrier matrix comprising a plurality of particles having non-concentric internally aqueous chambers containing a lipid-encapsulated drug to create an attached biotextile layer having a second compliance to thereby form a surgical mesh, wherein the first compliance and the second compliance differ by less than 20% (or less than 10, less than 30%, less than 40%, less than 50%, less than 10%, less than 5%, or less than 1%). A biotextile may be hydrated in any aqueous solution, such a biocompatible saline (e.g., half normal or normal saline with about 154 mEq/L or 77 mEq/L sodium and about 154 mEq/L or 77 mEq/L chloride or anything near or between these values, at pH 4.5 to 7.0 though other aqueous solutions may be used for the hydrating step). Some methods include the step of attaching a hydrogel to the biotextile layer and to the carrier matrix such that the hydrogel is between the biotextile layer and the carrier matrix. Some such methods include the step of swelling a hydrogel prior to the attaching a hydrogel step. Some methods include the step of diffusing a carrier matrix through a hydrogel, prior to, concomitant with, or after swelling the hydrogel. In some cases, a liposome may be coated with a hydrogel. In some methods the biotextile layer comprises one or more than one layer of collagen such as described elsewhere herein.

In a surgical repair graft as described herein, carrier matrix may be attached to one or more than one biotextile layer (e.g., be sandwiched in between two biotextile layers). Carrier matrix particles made by made by emulsifying lipids with an active agent, forming a suspension of multivesicular liposomes having a plurality of non-concentric chambers and including at least one amphipathic lips, at least one neutral lipid, and a therapeutic agent, or other methods. Carrier matrix particles may be formed any method or modifications of such methods, such as those described in US20100305500, US20110250264, US20130177633, US20130177634, US20130177636A, US20130177637, US20130195965, US20130209547, US20130306759A1, US20160206580, U.S. Pat. Nos. 9,205,052, 9,585,838, 9,724,302, 9,730,892, 9,737,482, 9,737,483, 9,757,336, 9,770,414, and 9,808,424.

Carrier matrix may be attached to a biotextile layer in islands or as a covering. In some examples, carrier matrix may be attached in islands, at a plurality of discrete attachment sites. Such an attachment site may correspond to a single particle or may correspond to a plurality of particles at that site and there may be one or more than one islands or attachment sites. Carrier matrix may form a depot of increased size. The size may be a depot of greater length or width and in some cases. In some cases carrier matrix may form a depot containing many particles agglomerated together and carrier matrix may not be a single layer. For example, such a depot may be 2, 3, 10, 20 or more particles high (e.g., perpendicular or more or less perpendicular to a plane defined by a biotextile layer. Carrier matrix may be attached to the one (or more than one) biotextile layer in a random configuration at a plurality of discrete attachment sites or in a regular configuration (regular pattern) at a plurality of discrete attachment sites. Some areas of a biotextile layer, such as along an edge, may be free or have less carrier matrix. In other examples, a region of a surgical repair graft that needs to bend may have fewer islands of carrier matrix or less carrier matrix to increase bendability in that region. In some cases, carrier matrix may be layer on over another material, such over a biotextile layer or over an adhesive layer. In may be layer in a solution or may be 3-printed. It may have a random pattern or a regular array pattern.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A surgical repair graft comprising:
   a plurality of stacked biotextile layers; and
   a bioabsorbable carrier matrix comprising multivesicular liposomes attached to at least one of the biotextile layers, wherein the multivesicular liposomes comprise a plurality of particles each having a plurality of non-concentric internally aqueous chambers each surrounded by a lipid membrane, at least one of the chambers and the lipid membrane containing an active agent, and wherein a first set of the chambers are on an exterior of the particles and a second set of chambers are on an interior of the particles, wherein lipid membranes on the first set of the chambers are configured to degrade before the lipid membranes on the second set of the chambers.

2. A surgical repair graft comprising:
   a plurality of stacked biotextile layers, wherein at least one biotextile layer comprises collagen; and
   a bioabsorbable carrier matrix comprising multivesicular liposomes attached to at least one of the biotextile layers, wherein the multivesicular liposomes comprise a plurality of particles each having a plurality of non-concentric internally aqueous chambers each surrounded by a lipid membrane, at least one of the aqueous chambers and the lipid membrane containing an active agent, and wherein a first set of the chambers are on an exterior of the particles and a second set of chambers are on an interior of the particles, wherein lipid membranes on the first set of the chambers are configured to degrade before the lipid membranes on the second set of the chambers.

3. The surgical repair graft of claim 2 wherein the internally aqueous chambers comprise the active agent.

4. The surgical repair graft of claim 2 wherein the lipid membrane comprises the active agent.

5. The surgical repair graft of claim 1 wherein the carrier matrix attached to the biotextile layer is discontinuous.

6. The surgical repair graft of claim 1 wherein the carrier matrix is attached to the biotextile layer at a plurality of discrete attachment sites.

7. The surgical repair graft of claim 1 wherein the carrier matrix is attached to the biotextile layer in a random pattern.

8. The surgical repair graft of claim 1 wherein the carrier matrix is attached to the biotextile layer at a plurality of discrete attachment sites in a fixed pattern.

9. The surgical repair graft of claim 1 wherein the carrier matrix comprises a covering.

10. The surgical repair graft of claim 1 wherein the carrier matrix comprises a covering having a plurality of openings.

11. The surgical repair graft of claim 1 wherein at least one biotextile layer has an open cell pore of between 0.5 mm and 6 mm diameter.

12. The surgical repair graft of claim 1 wherein the carrier matrix is between two of the biotextile layers.

13. The surgical repair graft of claim 1 wherein the active agent comprises an active pharmaceutical ingredient (API).

14. The surgical repair graft of claim 1 further comprising a polymer between the carrier matrix and the biotextile layer, the polymer adhering the carrier matrix to the biotextile layer.

15. The surgical repair graft of claim 1 further comprising a hydrogel between the carrier matrix and the biotextile layer, the hydrogel adhering the carrier matrix or the multivesicular liposomes to the biotextile layer wherein the hydrogel is chemically bonded, respectively to the carrier matrix or the multivesicular liposomes.

16. The surgical repair graft of claim 1 wherein a second of the biotextile layers is flexibly attached to a first of the biotextile layers with a pattern of discrete attachment sites having a density of attachment sites that is less than about 10 attachments/mm$^2$.

17. The surgical repair graft of claim 1 wherein a difference in bending stiffness of the surgical repair graft changes by less than 20% when the carrier matrix is adhered thereto compared with a bending stiffness of a similar surgical repair graft without carrier matrix.

18. The surgical repair graft of claim 1 wherein a difference in burst strength of the surgical repair graft changes by less than 20% when the carrier matrix is adhered thereto compared with the burst strength of a similar surgical repair graft without carrier matrix.

19. The surgical repair graft of claim 1 wherein a difference in surface roughness of the layers changes by less than 20% when the carrier matrix is adhered thereto compared with a burst strength of a similar surgical repair graft without carrier matrix.

20. A method for repairing an internal structure by the controlled release of an active agent from an implanted surgical repair graft, the method comprising:
    exposing a surgical repair graft having one biotextile layer or a plurality of stacked biotextile layers and a bioabsorbable carrier matrix attached to at least one of the one or plurality of stacked biotextile layers to an aqueous fluid, the carrier matrix comprising multivesicular liposomes, wherein the multivesicular liposomes comprise a plurality of particles each having a plurality of non-concentric internally aqueous chambers each surrounded by a lipid membrane, at least one of the chambers and the lipid membrane containing the active agent, wherein a first set of the chambers are on an exterior of the particles and a second set of chambers are on an interior of the particles; and
    degrading the carrier matrix over time by the aqueous fluid to thereby release the active agent from the carrier matrix, wherein lipid membranes on the first set of the chambers are degraded before the lipid membranes on the second set of the chambers.

21. The method of claim 20 wherein at least one of the one biotextile layer or plurality of biotextile layers comprises pores, the method further comprising flowing active agent from the carrier matrix through the pores to thereby release active agent to a body region adjacent the biotextile layer.

22. The method of claim 20 wherein a hydrogel is adhered to at least one of the layers, the method further comprising degrading the hydrogel.

23. The method of claim 20 wherein a compliance strain of the surgical repair graft is between 10-30% at 16 N/cm prior to the degrading step.

24. The method of claim 20 wherein the active agent comprises an active pharmaceutical ingredient (API).

25. The surgical repair graft of claim 1, wherein the plurality of stacked biotextile layers are stitched together.

26. The surgical repair graft of claim 1, wherein the plurality of stacked biotextile layers are adhered together with an adhesive.

* * * * *